United States Patent
Benetti et al.

(10) Patent No.: US 8,499,531 B2
(45) Date of Patent: Aug. 6, 2013

(54) SYSTEM AND METHOD FOR PACKAGING DENTAL INGOTS

(75) Inventors: Vince Benetti, Fairfield, CA (US); Wolfgang Ott, Antioch, CA (US)

(73) Assignee: Aalba Dent Inc., Fairfield, CA (US)

( * ) Notice: Subject to any disclaimer, the term of this patent is extended or adjusted under 35 U.S.C. 154(b) by 380 days.

(21) Appl. No.: 12/907,744

(22) Filed: Oct. 19, 2010

(65) Prior Publication Data
US 2012/0090272 A1    Apr. 19, 2012

(51) Int. Cl.
*B65B 11/50*    (2006.01)
*A61B 19/02*    (2006.01)

(52) U.S. Cl.
USPC ............... 53/397; 53/443; 53/461; 206/63.5

(58) Field of Classification Search
USPC ............. 53/397, 428, 443, 448, 461; 206/63.5
See application file for complete search history.

(56) References Cited

U.S. PATENT DOCUMENTS

| | | | | |
|---|---|---|---|---|
| 3,662,511 A | * | 5/1972 | Eliasberg | 53/411 |
| 3,708,945 A | * | 1/1973 | Klettke | 53/471 |
| 3,731,453 A | * | 5/1973 | Porteous | 53/471 |
| 4,154,795 A | * | 5/1979 | Thorne | 422/553 |
| 4,365,715 A | * | 12/1982 | Egli | 206/524.8 |
| 4,534,150 A | * | 8/1985 | Shirota | 53/390 |
| 4,549,656 A | * | 10/1985 | Barnes et al. | 206/589 |
| 4,813,211 A | * | 3/1989 | Treiber | 53/441 |
| 5,135,392 A | * | 8/1992 | Polansky | 433/37 |
| 5,203,450 A | * | 4/1993 | Benetti | 206/63.5 |
| 5,547,082 A | * | 8/1996 | Royer et al. | 206/725 |
| 6,059,111 A | * | 5/2000 | Davila et al. | 206/438 |
| 6,164,044 A | * | 12/2000 | Porfano et al. | 53/471 |
| 6,227,372 B1 | * | 5/2001 | Thomas et al. | 206/725 |
| 6,686,437 B2 | * | 2/2004 | Buchman et al. | 528/170 |
| 6,792,743 B2 | * | 9/2004 | Odell et al. | 53/452 |
| 7,322,480 B2 | * | 1/2008 | Bragadeste et al. | 206/599 |
| 7,428,807 B2 | * | 9/2008 | Vander Bush et al. | 53/425 |
| 7,937,907 B2 | * | 5/2011 | Fleckenstein et al. | 53/268 |
| 2003/0097182 A1 | * | 5/2003 | Buchman et al. | 623/18.11 |
| 2007/0157564 A1 | * | 7/2007 | Vander Bush et al. | 53/434 |
| 2008/0277091 A1 | * | 11/2008 | Beale et al. | 164/336 |
| 2009/0100802 A1 | * | 4/2009 | Bush et al. | 53/434 |
| 2009/0288794 A1 | * | 11/2009 | Lynn | 164/4.1 |
| 2009/0288973 A1 | * | 11/2009 | Hesseldahl | 206/366 |

* cited by examiner

*Primary Examiner* — Hemant M Desai
*Assistant Examiner* — Gloria R Weeks
(74) *Attorney, Agent, or Firm* — Stuart J. West; Shaun Sluman; West & Associates, A PC

(57) ABSTRACT

A method and system for producing, marking, and packaging ingots for use in fabricating dental prosthetics.

14 Claims, 29 Drawing Sheets

SYSTEM AND METHOD FOR PACKAGING DENTAL INGOTS

BACKGROUND

1. Field of the Invention

The present disclosure relates to the field of packaging of ingots, particularly those used for dental casting alloys and other applications.

2. Background

Several types of alloys are used in dental repair and reconstruction. Typically, these alloys are produced in ingots for convenient handling and storage in a dental laboratory. As these materials can be expensive, it is important for a dental laboratory to be able to easily monitor inventory, making sure that there is enough on hand to produce dental devices, while not maintaining a costly excess.

These alloys can have different compositions for suitability in different applications. However, sometimes it is not possible to differentiate different types of ingots themselves by physical inspection. Therefore, ingots are usually marked, by engraving, etching, or printing to indicate the alloy of which they are made. It is also important to keep the various types of ingots organized in the dental laboratory to facilitate producing dental devices and avoid confusion and potentially costly mistakes by using the incorrect alloy. Additionally, due to the high value of some of the materials and the values of some of the alloys provided by various sources of the ingots, methods and systems of identifying the source of and/or composition of the materials rapidly can prove valuable.

In addition, counterfeit ingots can enter the market, which can lead to inferior dental products for patients. Sometimes these imitations can be difficult to discern from the legitimate ingots. Therefore, it is also important to develop a production system that is difficult to copy without authorization.

What is needed is a system to efficiently produce and package ingots so that they can be safely transported and stored, neatly organized, and easily recognized in a dental laboratory to produce quality dental devices.

DETAILED DESCRIPTION

Figure 1:
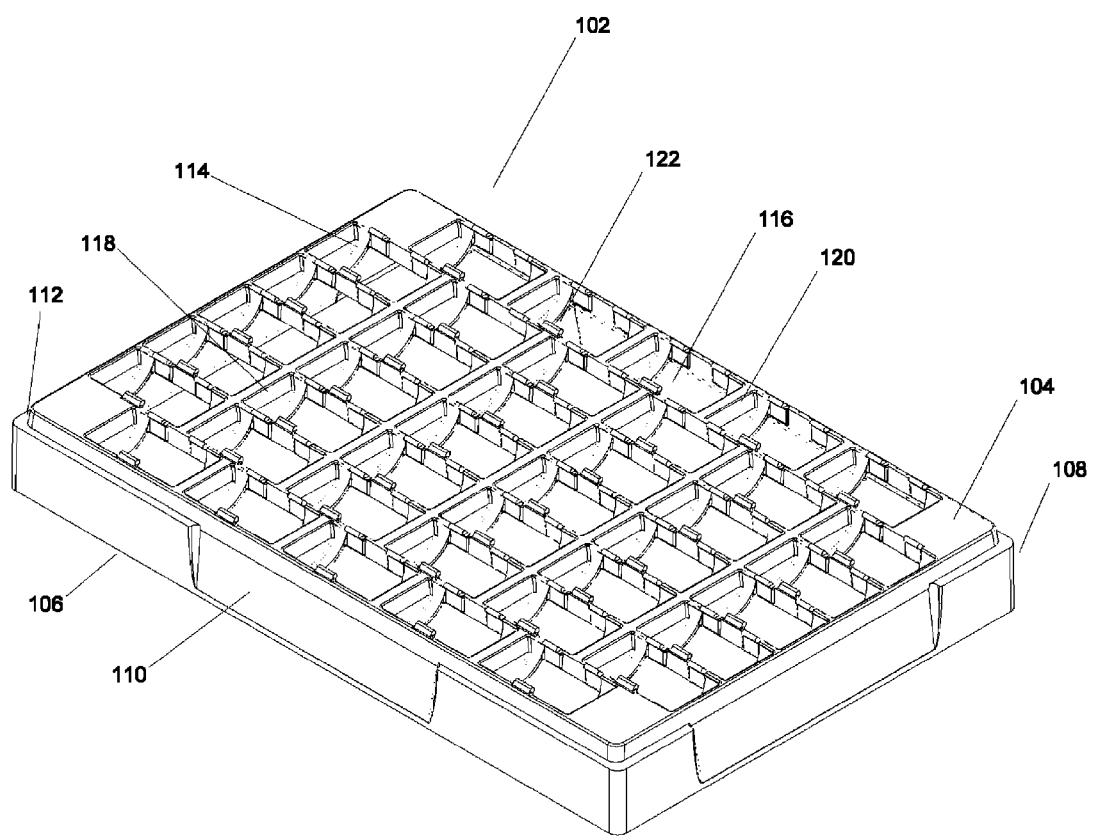
FIG. 1 depicts a perspective top view of one embodiment of a tray used in the present system.

FIG. 1 depicts a perspective view of one embodiment of a tray 102 that can be used in the present system. In some embodiments, a tray 102 can comprise a retaining surface 104 that can be elevated by a perimeter wall 106 extending substantially perpendicularly and downward from the edges of a retaining surface 104. As shown in FIG. 1, a retaining surface 104 can have a substantially rectangular geometry with slightly rounded corners, but in other embodiments can have any other known and/or convenient geometry.

As shown in the embodiment depicted in FIG. 1, a perimeter wall 106 can have thickened and/or recessed and/or counter-recessed and/or bulged and/or convex regions 108 at each corner extending partially along each adjacent exterior surface of a perimeter wall 106. In some embodiments, an area of a perimeter wall 106 located between thickened regions 108 can be marked with text, a logo, or any other desired indicia 110.

In some embodiments, a perimeter wall 106 can extend slightly outward from a retaining surface 104, while thickened regions 108 can have an exterior surface substantially orthogonal to a retaining surface 104. As shown in FIG. 1, this can create a lip 112 along the top of a thickened region 108, slightly below a retaining surface 104.

A retaining surface 104 can further comprise a plurality of cells 114, which, in some embodiments, can each have a geometry so as to selectively engage with a dental alloy ingot. As shown in FIG. 1, a cell 114 can have a substantially rectangular longitudinal cross-sectional geometry, but in other embodiments can have any other known and/or convenient geometry. As shown in FIG. 1, a plurality of cells 114 can be arranged adjacently and substantially linearly, but in other embodiments can have any other known and/or convenient arrangement.

As shown in the embodiment of FIG. 1, cells 114 can be arranged in a 5×6 grid pattern with an additional row of 5 cells 114 on each lateral side, which can be staggered relative to the central 5×6 grid of cells 114 to leave substantially square regions at the corners of a retaining surface 104. However, in other embodiments, cells 114 can be arranged in any other known and/or convenient pattern.

Figure 1A:
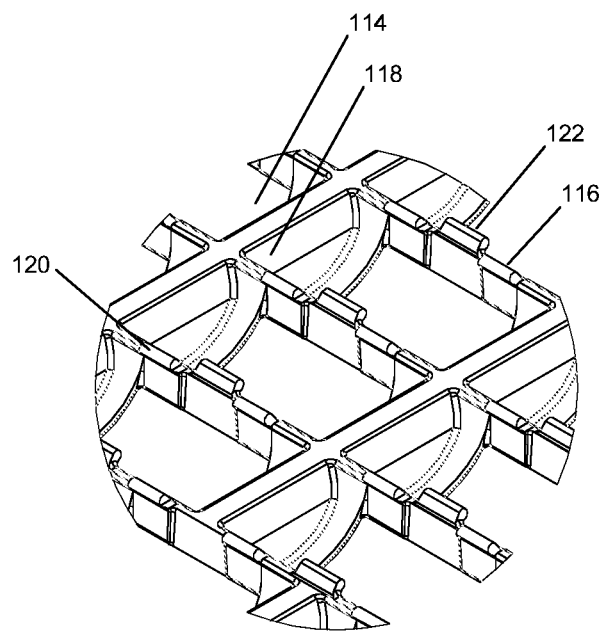
FIG. 1a depicts a perspective detail view of the tray embodiment shown in FIG. 1.

In some embodiments, as shown in FIG. 1a, a cell 114 can have a pair of substantially parallel longitudinal members 116 that can extend downward from a retaining surface 104. A cell 114 can have a pair of end members 118 that can extend downward from a retaining surface 104. End members 118 can be connected to and substantially orthogonal to a pair of substantially parallel longitudinal members 116 so as to form a substantially rectangular opening to a cell 114 substantially in the plane of a retaining surface 104. As shown in FIG. 1a, an end member 118 can have a substantially semicircular geometry with the diameter substantially coinciding with the interior width of a cell 114 and the curved portion extending downward from a retaining surface 104. In some embodiments, at least one transverse member 120 can extend between and connect to the lower edges of a pair of substantially parallel longitudinal members 116, having one edge connected along the lower curve of an end member 118. In some embodiments, a transverse member 120 can have a width not exceeding approximately half of the length of a cell 114, and each transverse member 120 can have approximately the same width. However, in other embodiments, each transverse member 120 can have a different width. As shown in FIG. 1, in embodiments having transverse members 120 each of a width less than approximately half of the length of a cell 114, the underside of a cell 114 can remain open to permit access to an ingot from this side.

Figure 1B:
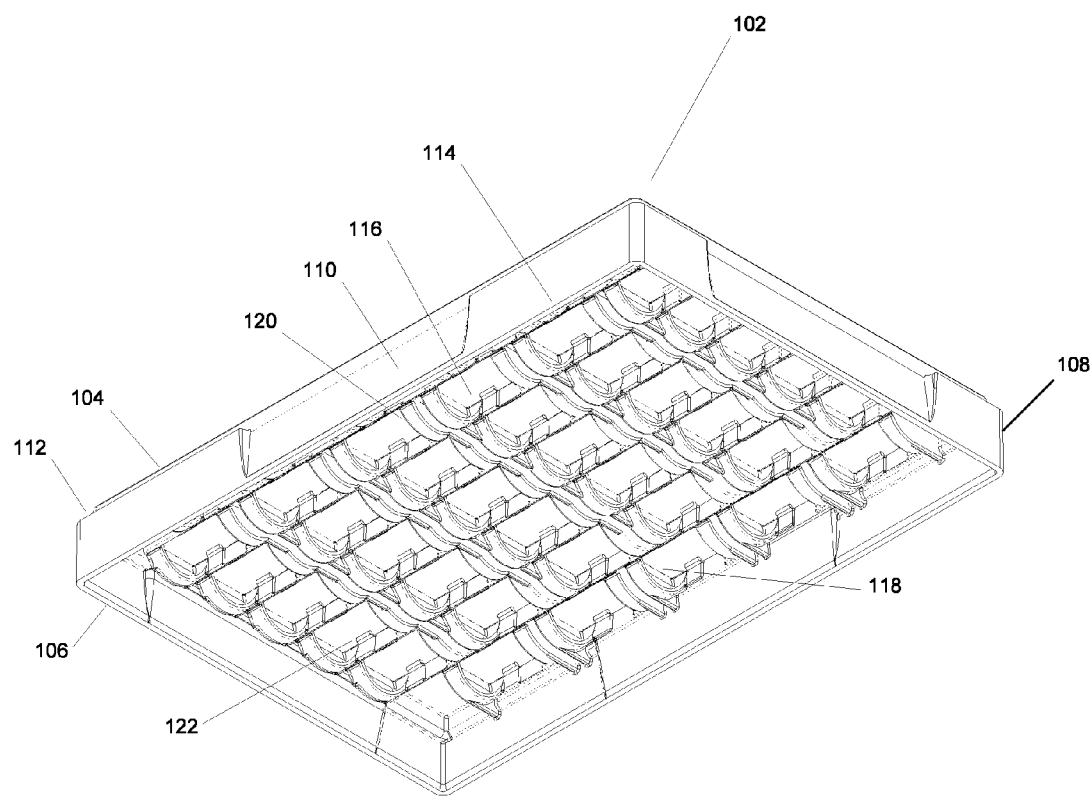
FIG. 1b depicts a perspective bottom view of one embodiment of a tray used in the present system.

As shown in FIGS. 1a and 1b, a cell 114 can have a substantially semi-cylindrical interior cross-sectional geometry. In such embodiments, a substantially cylindrical dental alloy ingot can selectively engage with a cell 114 such that a longitudinal portion of an ingot remains above a retaining surface 104 when occupying a cell 114. However, in other embodiments, a cell 114 can have any other known and/or convenient interior cross-sectional geometry to selectively engage with a desired dental alloy ingot.

Figure 1C:
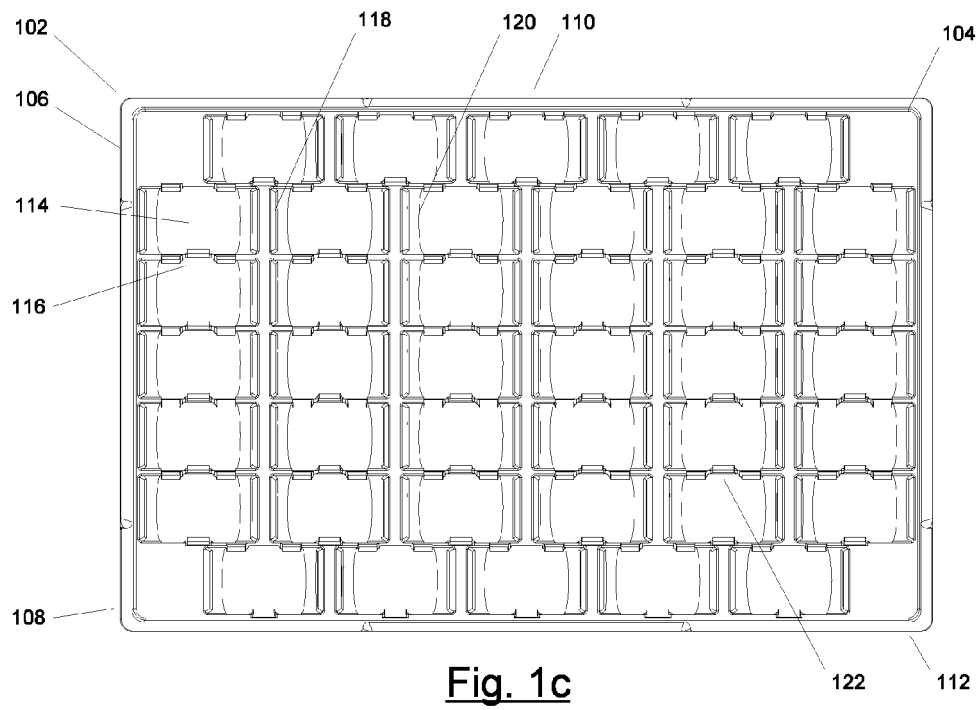
FIG. 1c depicts a top planar view of one embodiment of a tray used in the present system.

In some embodiments, as shown in FIGS. 1, and 1a-1d, at least one tab 122 can extend from the top edge of a substantially parallel longitudinal member 116 above a retaining surface 104, and toward the interior of a cell 114. In some embodiments, as shown in FIG. 1c, three tabs 122 can extend from the top edge of a substantially parallel longitudinal member 116, such that one tab 122, located substantially at the midpoint of a substantially parallel longitudinal member 116, can extend over one cell 114, while two flanking tabs 122 can extend over a laterally adjacent cell 114.

Figure 1D:
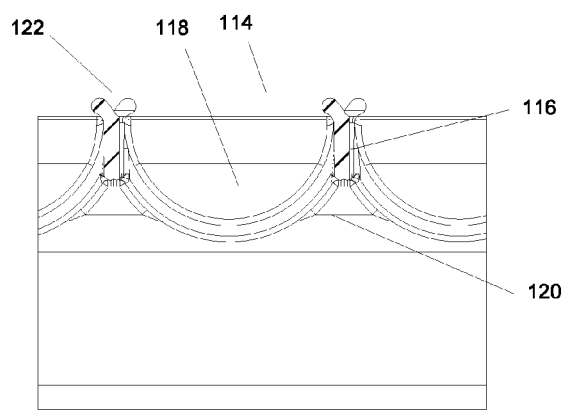
FIG. 1d depicts a detail transverse cross-sectional view of the embodiment shown in FIG. 1.

As shown in FIG. 1d, a tab 122 can have an angle of approximately 45-degrees, and/or any other known and/or convenient angle while extending above the top of a retaining surface 104, but in other embodiments can be positioned at any other known and/or convenient angle. In some embodiments one or more of the tabs 122 can be adapted and designed to have any desired length and/or flexibility and/or stiffness relative to a longitudinal member 116 and/or any other known and/or convenient element and/or item. In some embodiments, a tab 122 can have a thickness substantially similar to that of a substantially parallel longitudinal member 116. In some embodiments, as shown in FIG. 1d, a tab 122 can have a substantially rounded top edge, but in other embodiments can have any other known and/or convenient geometry. In some embodiments the tab 122 can be thinner than, the same thickness as or thicker than the longitudinal member 116, and/or can have any other known and/or convenient and/or desired thickness.

In some embodiments, a tray 102 can be injection molded from copolymer polypropylene, but in other embodiments can be produced by any other known and/or convenient method and with any other known and/or convenient material. In some embodiments, a material used in forming a tray 102 can have any known and/or convenient properties desirable to meet specified design criteria.

In use, an ingot can be placed horizontally into a cell 114. In embodiments such as those shown in FIG. 1, in which a cell 114 can be configured to hold a substantially cylindrical ingot, end regions of said ingot can rest on transverse members 120. Substantially half of an ingot can lie below the top edge of a cell 114, while tabs 122 can secure an ingot in a cell 114 by extending above the top edge of a cell 114 and substantially adjacent to the surface of an ingot lying above the top edge of a cell 114. In such embodiments, ingots can remain secured in cells 114 regardless of the position of a tray 102 (e.g., upside-down). Further, in such embodiments, portions of the lateral surface of an ingot can remain accessible via both the top and bottom of a retaining surface 104.

As a tray 102 is filled, ingots in adjacent cells 114 can apply minimal lateral forces to laterally adjacent cells 114. As a result, although the holding force of tabs 122 can vary slightly with the number of filled laterally adjacent cells 114, ingots can be securely held in any of cells 114 regardless of the number of filled cells 114 versus empty cells 114. As a result, a user can handle a partially filled tray 102 without the risk of ingots falling out of cells 114.

To remove an ingot from a tray 102, a user can apply a force directly to an ingot from the underside of the retaining surface 104, through the bottom of a cell 114 between transverse members 120, causing tabs 122 to momentarily flex away from the lateral centerline of a cell 114 and release an ingot.

Figure 2:
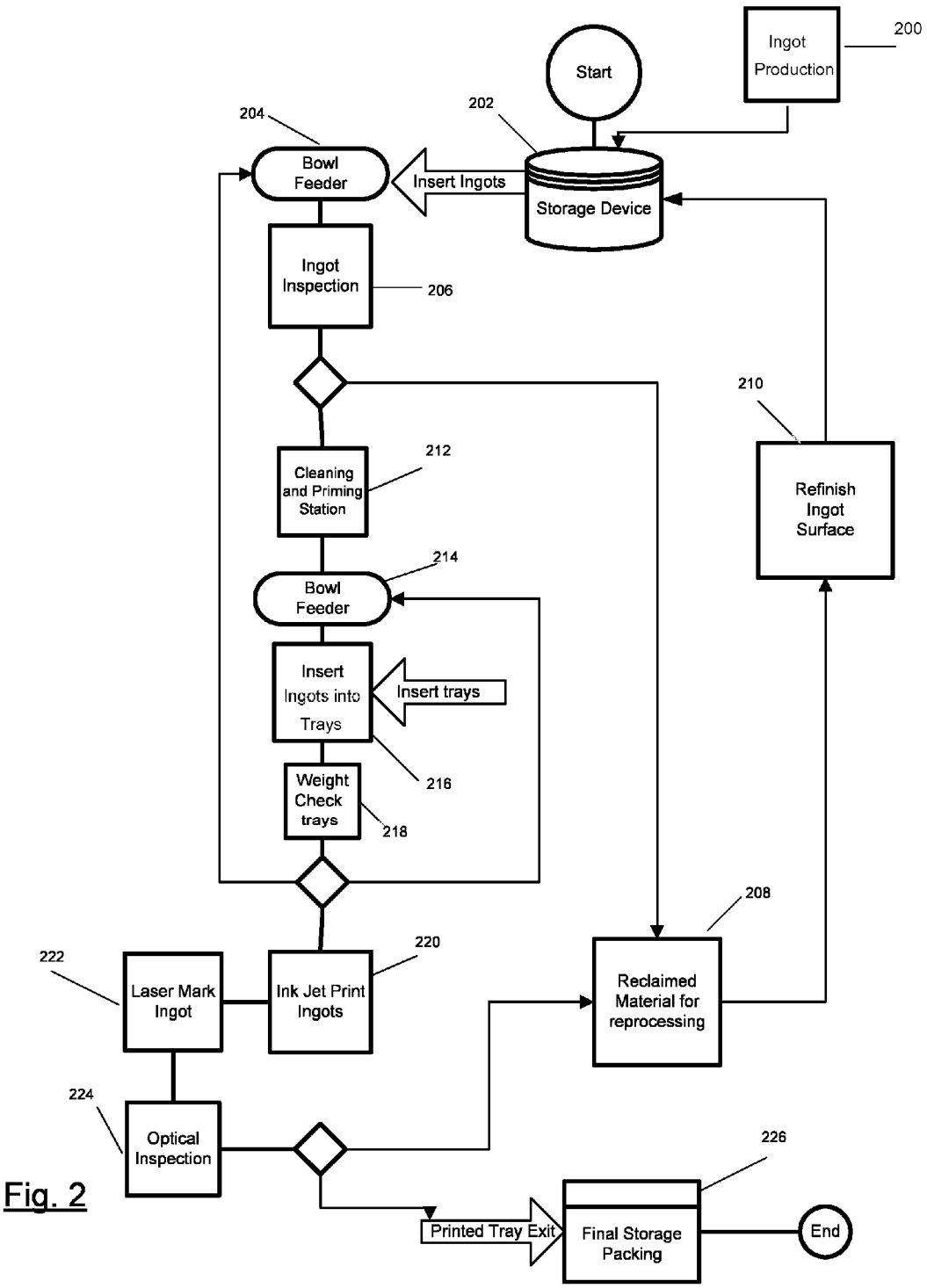
FIG. 2 depicts a flow chart giving an overview of an embodiment of the present system.

FIG. 2 is a flow chart depicting an overview of one embodiment of a production line of the present system that can comprise the following steps. In some embodiments, ingots can be produced by continuous casting or any other known and/or convenient method herein referred to as ingot production 200 and stored in any known and/or convenient storage device 202. Ingots can be introduced to the system via a first bowl feeder 204 or any other known and/or convenient mechanism.

Ingots can be inspected for compliance with required size, mass, weight, cosmetics, or any other known and/or convenient parameters at an inspection station 206. Ingots failing inspection can be transferred to a material reclamation unit 208, where ingots can be reprocessed. From there, ingots can be transferred to an ingot surface refinishing station 210, where upon refinishing ingots can be transferred back to a storage device 202 and/or they can be returned to the Ingot Production Process 200. Ingots passing inspection can then be transferred to a cleaning and priming station 212, and then enter a second bowl feeder 214 or any other known and/or convenient mechanism. In some embodiments, an ingot inspection rate can be approximately 80,000 ingots/day (±16,000 . . . ). However, in alternate embodiments any other known and/or convenient range and/or known and/or convenient and/or desired±limitation/variation/variance can be implemented.

Ingots can then pass from a second bowl feeder 214 to an ingot-tray insertion station 216. Trays 102 can be introduced to a tray insertion station 216 via a stack-feed, linear-feed, or any other known and/or convenient mechanism. Ingots can then be inserted into trays 102 at a rate of approximately 300 trays/hr (±60 . . . ). However, in alternate embodiments, any other known and/or convenient range and/or known and/or convenient and/or desired±limitation/variation/variance can be implemented.

Loaded trays 102 can then advance to a weight-check station 218. Loaded trays can be weighed to check compliance with a desired weight range, which in some embodiments can be 200 gram (±4 grams . . . ) and/or any other known and/or convenient and/or desired weight range and/or known and/or convenient and/or desired±limitation/variation/variance. Loaded trays 102 passing weight inspection can then advance to a first marking station 220. Loaded trays failing weight inspection can be unloaded and the ingots returned to either a first bowl feeder 204 or a second bowl feeder 214.

At a first marking station 220, ingots loaded into a tray 102 can be individually marked via inkjet printing, pad printing, stamping, engraving, etching, or any other known and/or convenient method. In some embodiments of the present system, a loaded tray 102 can be inserted into an inkjet printer such that the portion of each ingot's lateral surface that faces upward and is accessible from the top of a tray 102 can be printed with a desired indicia, text, or image. In embodiments employing inkjet printing as a marking method, trays can be processed at a rate of 150 trays/hour (±30 . . . ) or any other known and/or convenient range.

Loaded trays 102 bearing marked ingots can then travel to a second marking station 222. Here, the lateral side of an ingot accessible from the underside of a retaining surface (i.e., opposite the previously marked ingot surface) can be laser marked and/or marked via any other known and/or convenient method.

Following marking, loaded trays 102 of ingots can proceed to an optical inspection station 224. Loaded trays can be inspected at a rate of approximately 300 trays/hour (±60 . . . ) or any other known and/or convenient range. Loaded trays 102 passing optical inspection can then advance to a storage device 202 and then final packaging 226. Loaded trays 102 failing optical inspection can be unloaded and the ingots sent to a reclamation unit 208 for reprocessing. In some embodiments optical inspection can be performed by a trained person who would make a subjective evaluation/determination of the marks quality based upon a pre-approved standard. However, in alternate embodiments, the optical inspection can be performed by an automated computer based system which has been programmed to adhere to a minimum acceptance standard.

Figure 2A:
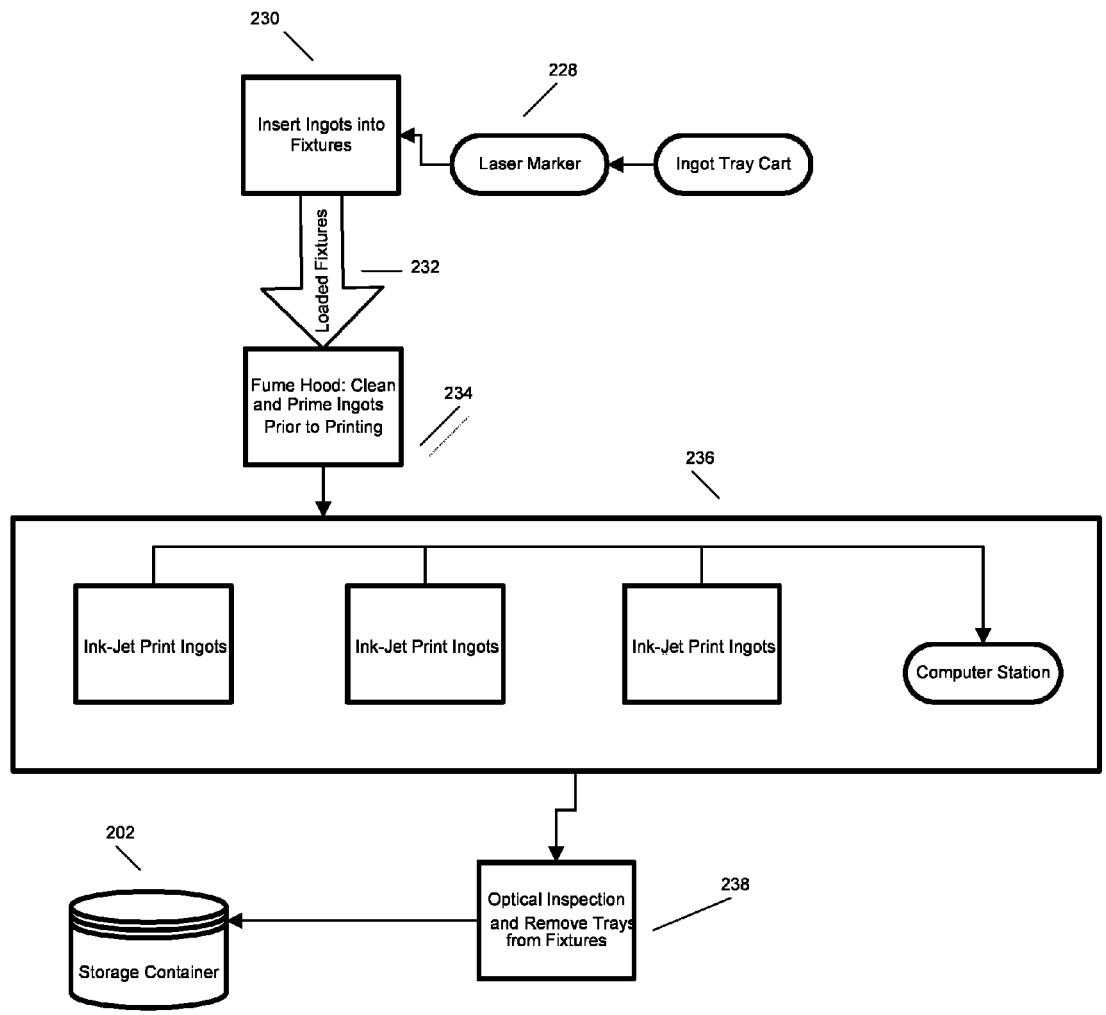
FIG. 2a depicts a detail view of the printing process in one embodiment of the present system

FIG. 2a depicts a flow chart detail of a laser marking/inkjet printing process used in one embodiment of the present system. Loaded trays 102 can be placed into a laser marking system 228 where they can be marked with desired indicia, text, or image. In some embodiments, loaded trays 102 can then be placed into fixtures 230 which can contain 15 trays (+/−5) and/or any other known and/or convenient number having any known and/or convenient configuration. In the embodiment depicted in FIG. 2a, loaded fixtures 232 can then be cleaned and primed via a manual wiping process 234 and/or via any other known and/or convenient cleaning process. In the embodiment depicted in FIG. 2a, cleaned and primed loaded fixtures 232 can be placed into the inkjet printing process 236 where the ingots can be marked with desired indicia, text, or image. In some embodiments, upon exiting the inkjet printing process 236, the loaded trays 102 can be removed from the loaded fixture 232 and visually inspected 238 for defects. However, the loaded fixture 232 and the ingots can be inspected 238 without being removed from the fixture 232. If the tray 102 is deemed acceptable, it can be placed into storage 202 and await final packaging 226 and/or can proceed directly to final packaging 226. If the tray is deemed unacceptable, the tray 102 can be rejected, in-whole or in-part, and can be, in-whole or in-part, submitted to reclaimed material 208 for reprocessing and further ingot production 200. In some embodiments, the empty fixture 230 can then be returned to the beginning of the process.

Figure 3:
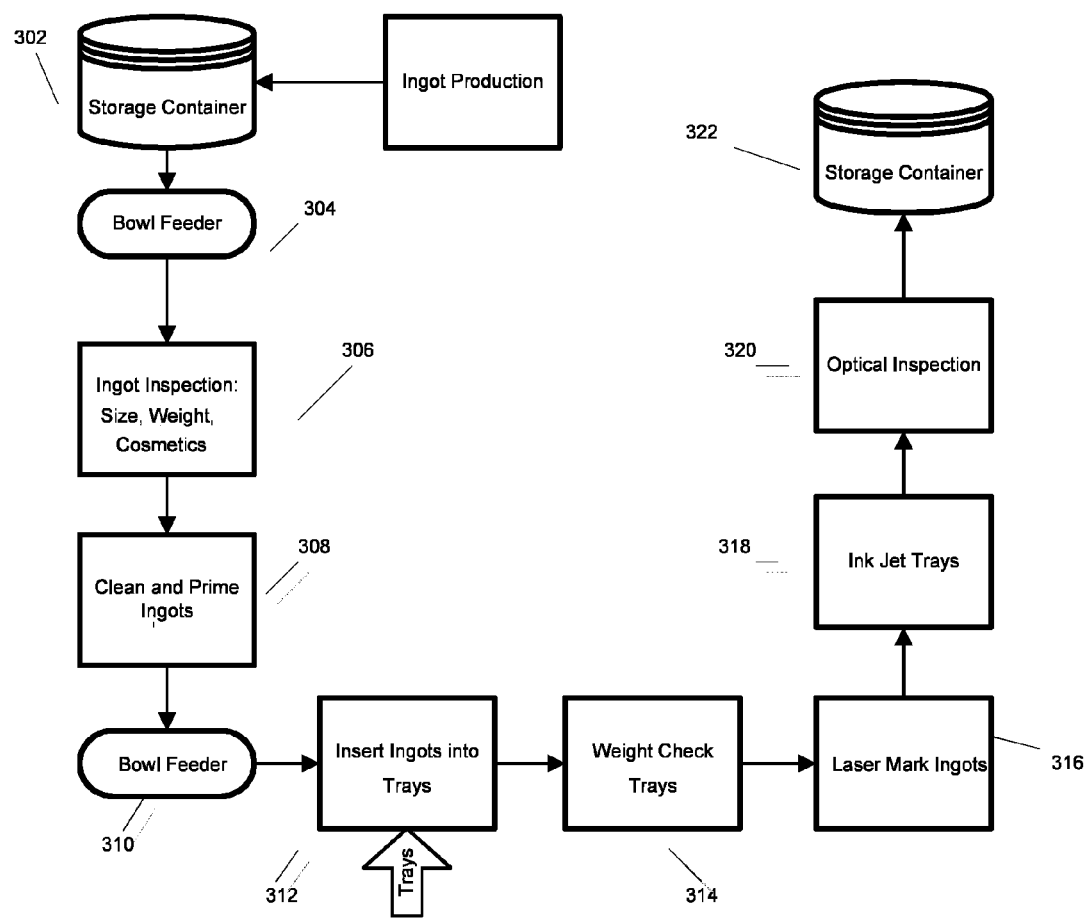
FIG. 3 depicts a flow chart giving an alternate embodiment of the present system.

FIG. 3 depicts a flow chart overview of an alternative embodiment of the present system that can comprise the following steps. In some embodiments, ingots can be produced by continuous casting or any other known and/or convenient method herein referred to as ingot production 300 and stored in any known and/or convenient storage device 302. Ingots can be introduced to the system via a first bowl feeder 304 or any other known and/or convenient mechanism.

Ingots can be inspected for compliance with required size, mass, weight, cosmetics, or any other known and/or convenient parameters at an inspection station 306. Ingots passing inspection can then be transferred to a cleaning and priming station 308, and then enter a second bowl feeder 310 or any other known and/or convenient mechanism. In some embodiments, an ingot inspection rate can be approximately 100,000 ingots/day (±20,000) or any other known and/or convenient range and/or known and/or convenient and/or desired±limitation/variation/variance can be implemented.

Ingots can then pass from a second bowl feeder 310 to an ingot-tray insertion station 312. Trays 102 can be introduced to a tray insertion station 312 via a stack-feed, linear-feed, or any other known and/or convenient mechanism. Ingots can then be inserted into trays 102 at a rate of approximately 300 trays/hr (±60) or any other known and/or convenient range.

Loaded trays 102 can then advance to a weight-check station 314. Loaded trays can be weighed to check compliance with a desired weight range, which in some embodiments can be 200 grams (±4 grams) and/or any other known and/or convenient and/or desired weight range and/or known and/or convenient and/or desired±limitation/variation/variance. Loaded trays 102 passing weight inspection can then advance to a first marking station 316.

At a first marking station 316, the lateral side of an ingot accessible from the underside of a retaining surface (i.e., opposite the previously marked ingot surface) can be laser marked, or marked employing any other known and/or convenient marking method and/or system. Laser-marked ingots can then be transferred to a second marking station 318.

At a second marking station 318, ingots loaded into a tray 102 can be individually marked via inkjet printing, pad printing, stamping, engraving, etching, or any other known and/or convenient method. In some embodiments of the present system, a loaded tray 102 can be inserted into an inkjet printer such that the portion of each ingot's lateral surface that faces upward and is accessible from the top of a tray 102 can be printed with a desired indicia, text, or image. In embodiments employing inkjet printing as a marking method, trays can be processed at a rate of 300 trays/hour (±60) or any other known and/or convenient range and/or known and/or convenient and/or desired±limitation/variation/variance can be implemented.

Following marking, loaded trays 102 of ingots can proceed to an optical inspection station 320. Loaded trays can be inspected at a rate of approximately 300 trays/hour (±60) or any other known and/or convenient range and/or known and/or convenient and/or desired±limitation/variation/variance can be implemented. Loaded trays 102 passing optical inspection can then advance to a storage unit 322.

Figure 4:
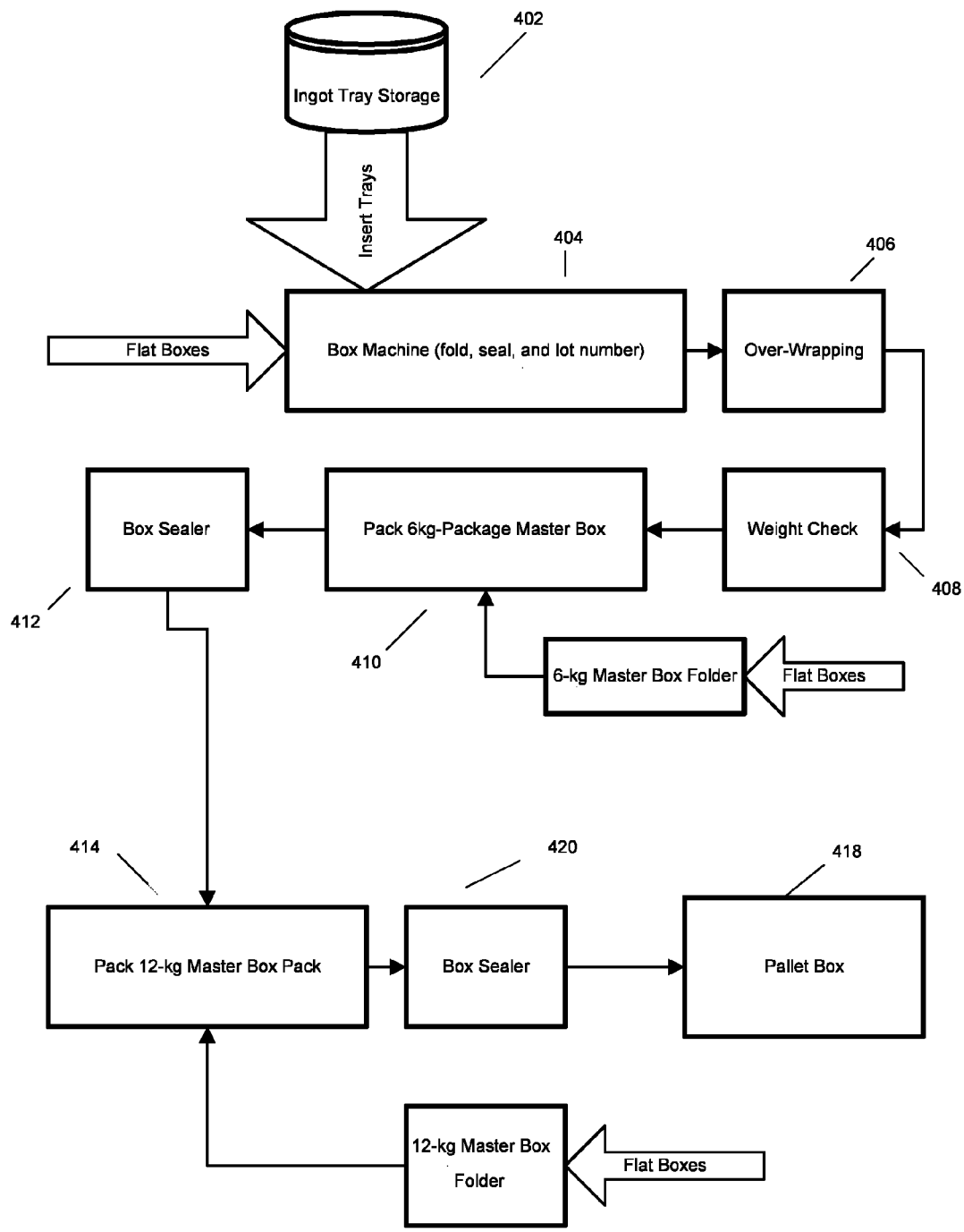
FIG. 4 depicts a flow chart giving an overview of an embodiment of the packaging process in the present system.

FIG. 4 depicts a flow chart showing an overview of a packaging segment of an embodiment of the present system. Loaded trays 102 of marked ingots can be transferred to an ingot tray storage device 402 to await packaging. In a box machine 404, loaded trays 102 of marked ingots are placed into pre-folded boxes, which are then sealed around each loaded tray 102. In some embodiments, a box machine can box a loaded tray at a rate of approximately 300 packages/hr (±60) or any other known and/or convenient rate and/or known and/or convenient and/or desired±limitation/variation/variance can be implemented. In a box machine 404, the exterior surface of a sealed box can be marked via printing, adhesive label, or any other known and/or convenient method. Such marking can include information relating to dates of manufacture, serialization, lot numbers or any other known and/or convenient information relating to production and authentication of the ingots enclosed.

Sealed boxes can then be transferred to an overwrapping station 406 where they can be wrapped with a plastic, cellophane, paper, or any other known and/or convenient type of overwrapping. Wrapped boxes can then be transferred to a weight-check station 408. Wrapped individual boxes passing inspection can then be transferred to a master box station 410, where individual boxes are grouped and packed into larger units.

At a first master boxing station 410, individual boxes can be placed into a first master box and then sent to a box sealing station 412.

As shown in FIG. 4, the multiple-pack master boxes can be grouped together and sent to a second master boxing station 414 for further consolidation. However, in other embodiments, first master boxes can be grouped into any other known and/or convenient units.

At a second master boxing station 414, individual boxes can be placed into a second master box and then sent to a final box sealing station 416. The larger master boxes can then be sent to a pallet box 418 and grouped into any known and/or convenient quantity for shipping.

An ancillary benefit of the present system is that it can deter counterfeit activities by creating a production process that can be very difficult to duplicate. In some embodiments, additional authentication measures can be taken, such as marking with identification and serialization indicia.

In some embodiments, further authentication can be provided by laser marking and/or marking ingots with a logo, text, or a serial number using any known and/or convenient marking method, apparatus and/or system. In addition, a tray 102 can also be marked via printing, an adhesive label, or any other known and/or convenient method. A box enclosing a loaded tray 102, as well as external wrapping on a box can likewise be marked with such indicia.

In some embodiments the markings can be used to establish authenticity of the ingots. In some embodiments, the individual ingots can be marked with first indicia, the tray 102 can be marked with a second indicia and the exterior packaging can be marked with a third indicia. In some embodiments, the first indicia, second indicia and third indicia can be related in any known and/or convenient manner and/or unrelated and/or randomized. In some embodiments, the first, second and third indicia can be used either individually and/or collaboratively to establish authenticity of the ingots. In alternate embodiments, a user can verify at least one of the first, second and third indicia to establish authenticity via communication with an authentication service and/or authentication method.

Figure 5:
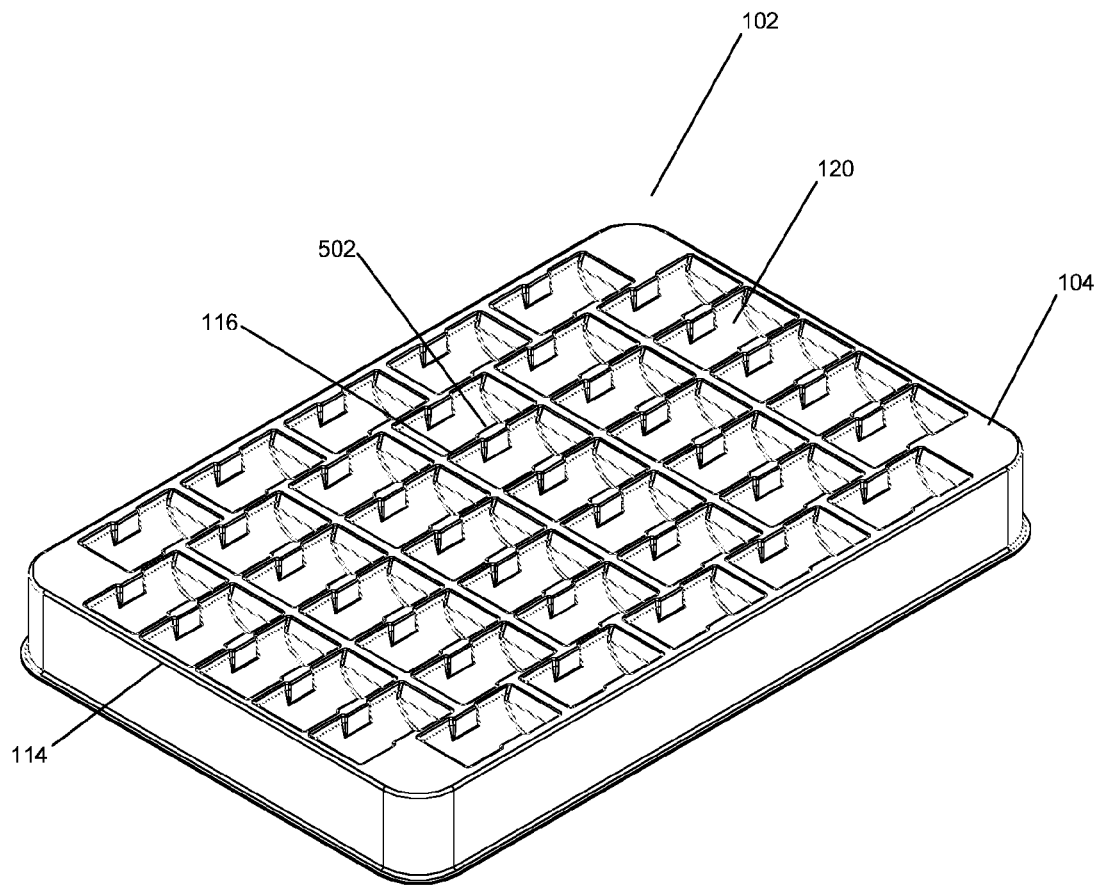
FIG. 5 depicts a perspective view of another embodiment of a tray used in the present system.

FIG. 5 depicts a perspective view of another embodiment of a tray 102 that can be used in the present system. In such embodiments, a transverse member 120 can substantially completely enclose the underside of cell 114.

Figure 5A:
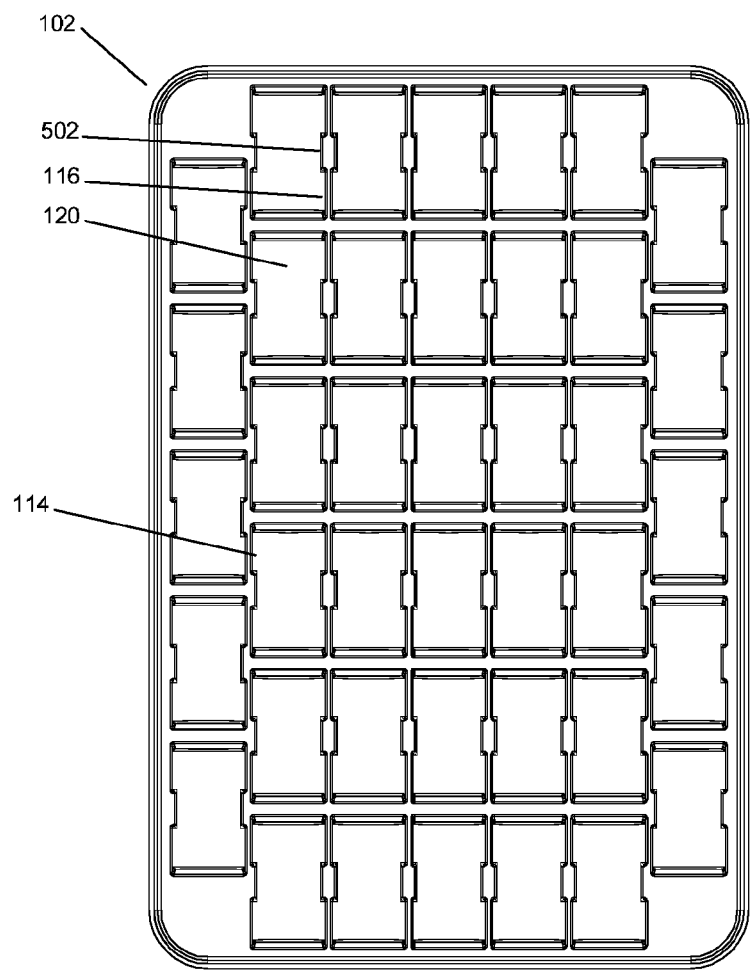
FIG. 5a depicts top planar view of the embodiment of a tray used in the present system as shown in FIG. 5
Figure 5B:
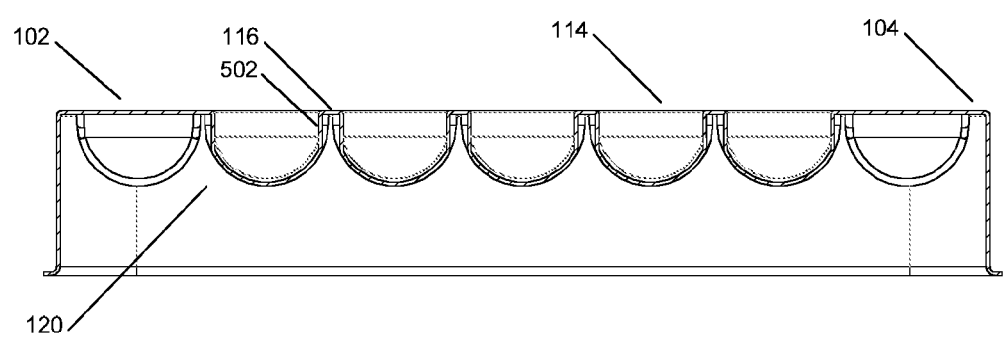
FIG. 5b depicts a detail transverse cross-sectional view of the embodiment shown in FIG. 5.

As shown in FIG. 5, a longitudinal member 116 can have a bilaterally raised region 502 located substantially at the midpoint of the top edge of a longitudinal member 116 such that each raised region extends into adjacent cells 114 sharing a substantially parallel longitudinal member 116. As shown in FIG. 5a, a raised region 502 can extend slightly toward the longitudinal midline of a cell 114. As shown in FIG. 5b, the top edge of a raised region 502, can be coincident with the top of a retaining surface 104 so as not to extend over the top edge of a cell 114.

Embodiments such as those depicted in FIG. 5 can be vacuum-formed from a polymer or any other known and/or convenient material. In some embodiments a material can be substantially translucent, but in other embodiments, can be substantially transparent or opaque. In some embodiments, a material can have any known, convenient and/or desired strength and/or flexibility.]

In use, an ingot can be placed into a cell 114 such that raised regions 502 can hold the ingot in place. In embodiments such as those shown in FIG. 5, in which a cell 114 can be configured to hold a substantially cylindrical ingot, an ingot can rest horizontally in a cell 114 such that substantially half of an ingot lies below the top edge of a cell 114 and raised regions 502 can apply a substantially lateral force applied substantially at an ingot's longitudinal midpoint to hold the ingot in place. As a tray 102 is filled, ingots in adjacent cells 114 can apply lateral forces to laterally adjacent cells 114. As a result, the holding force of raised regions 502 can increase slightly with the number of filled laterally adjacent cells 114. However, even if a tray 102 is partially filled, sufficient lateral force exists each in cell 114 to secure an ingot in place.

To remove an ingot, a user can apply an exterior force directed substantially toward the longitudinal midline of an ingot to the bottom surface of a cell 114, causing a transverse member 120 to deform slightly toward an ingot and substantially parallel longitudinal members 116 to momentarily flex laterally outward, increasing the distance between raised regions 502 to subsequently release an ingot, as it is pushed upward out of a cell 114.

Figure 6:
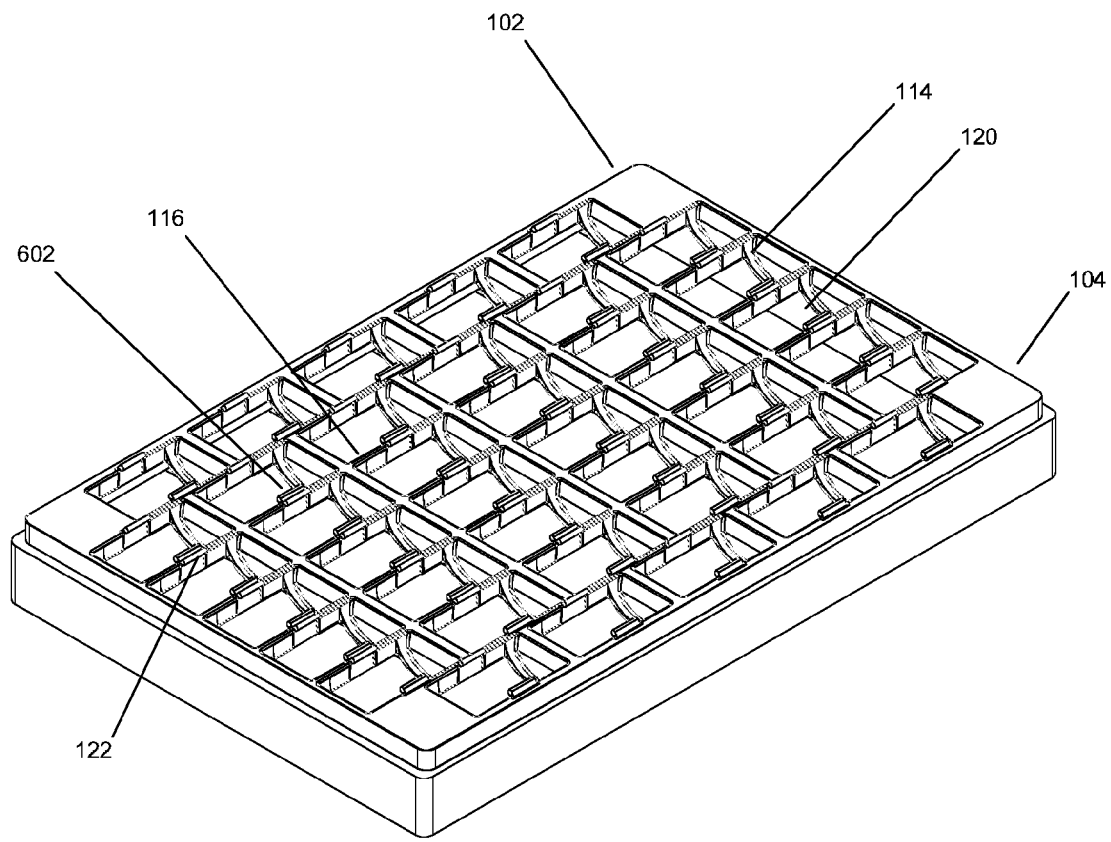
FIG. 6 depicts a perspective view of another embodiment of a tray used in the present system.
Figure 6A:
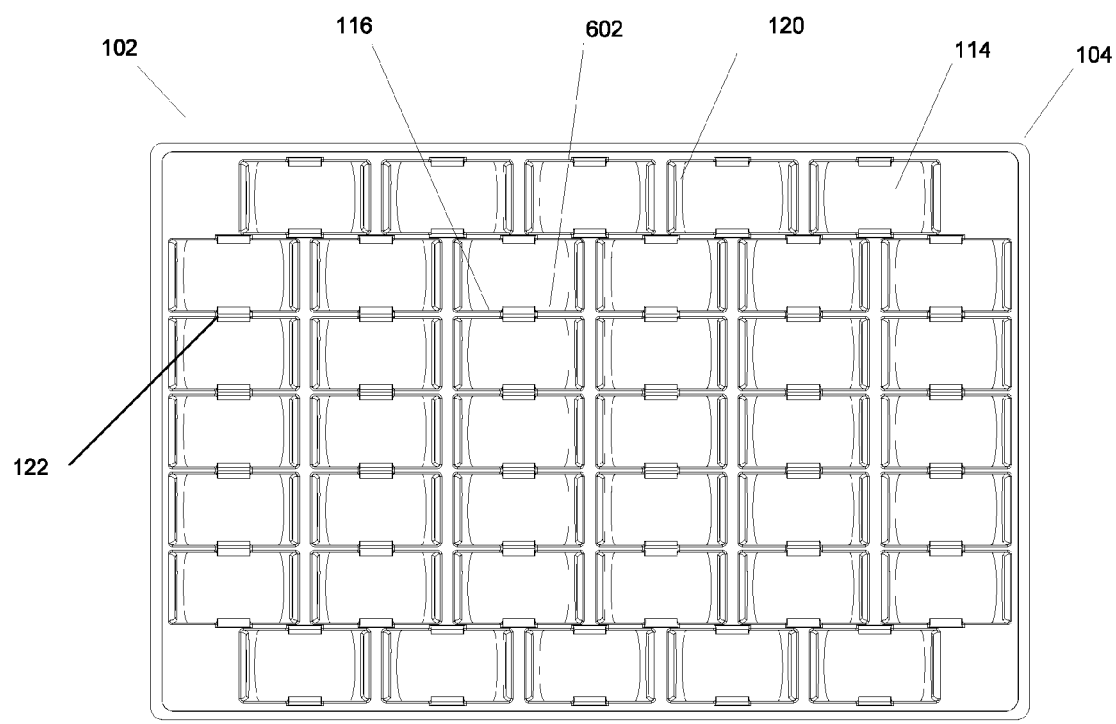
FIG. 6a depicts top planar view of the embodiment of a tray used in the present system as shown in FIG. 6.
Figure 6B:
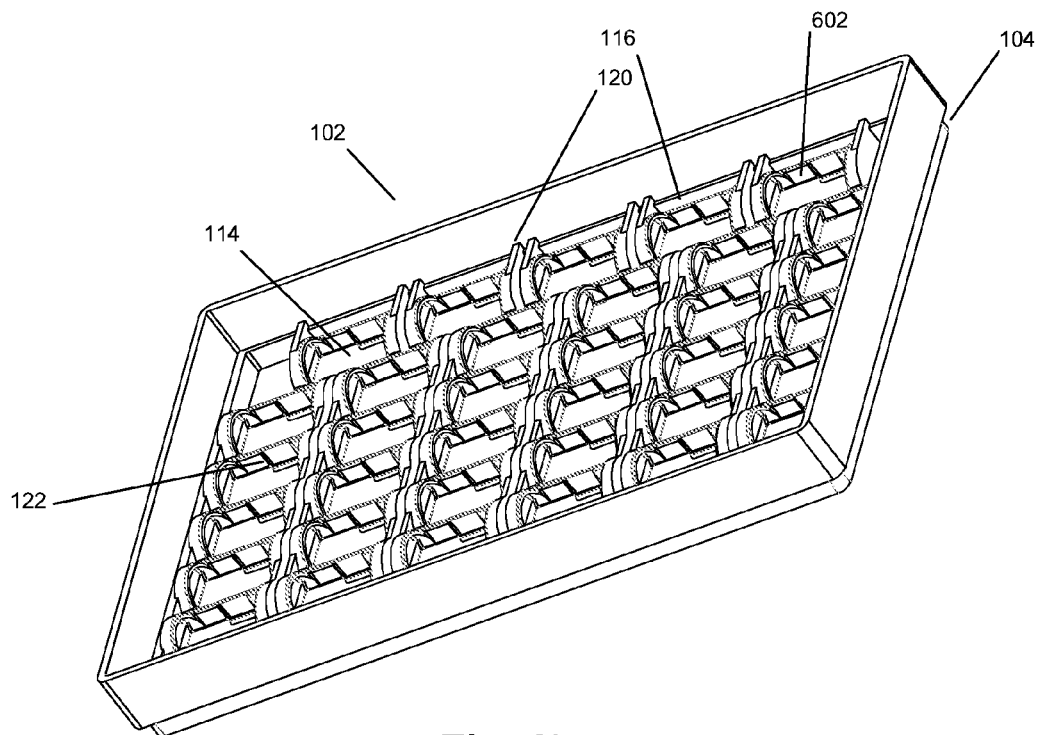
FIG. 6b depicts a perspective bottom view of the embodiment of a tray used in the present system as shown in FIG. 6.

FIG. 6 depicts a perspective view of another embodiment of a tray 102 that can be used in the present system. In some embodiments, as shown in FIG. 6, a pair of laterally adjacent tabs 602 can extend from substantially the midpoint of the top edge of a longitudinal member 116 with each extending toward the interior of a laterally adjacent cell 114.

Figure 6C:
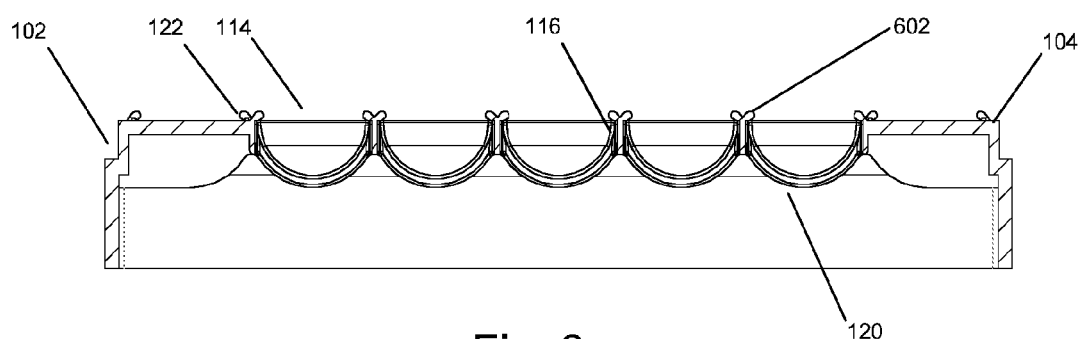
FIG. 6c depicts a detail transverse cross-sectional view of the embodiment shown in FIG. 6.

As shown in FIG. 6, each laterally adjacent tab 602 can have an angle of approximately 45-degrees and/or any other known, convenient and/or desired angle while extending above the top of a retaining surface 104, but in other embodiments can be positioned at any other known and/or convenient angle. In some embodiments one or more of the tabs 122 can be adapted and designed to have any desired length and/or flexibility and/or stiffness relative to a longitudinal member 116 and/or any other known and/or convenient element and/or item. In some embodiments, a laterally adjacent tab 602 can have a thickness substantially similar to that of a substantially parallel longitudinal member 116. In some embodiments, as shown in FIG. 6c, a laterally adjacent tab 602 can have a substantially rounded top edge, but in other embodiments can have any other known and/or convenient geometry.

In use, an ingot can be placed horizontally into a cell 114. In embodiments such as those shown in FIG. 6, in which a cell 114 can be configured to hold a substantially cylindrical ingot, end regions of said ingot can rest on transverse members 120. Substantially half of an ingot can lie below the top edge of a cell 114, while laterally adjacent tabs 602 can secure an ingot in a cell 114 by extending above the top edge of a cell 114 and substantially adjacent to the surface of an ingot, positioned substantially at the transverse midpoint of an ingot lying above the top edge of a cell 114. In such embodiments, ingots can remain secured in cells 114 regardless of the position of a tray 102 (e.g., upside-down). Further, in such embodiments portions of the lateral surface of an ingot remain accessible via both the top and bottom of a retaining surface 104.

As a tray 102 is filled, ingots in adjacent cells can apply minimal lateral forces to laterally adjacent cells 114. As a result, although the holding force of laterally adjacent tabs 602 can vary slightly with the number of filled laterally adjacent cells 114, ingots can be securely held in any of cells 114 regardless of the number of filled cells 114 versus empty cells 114. As a result, a user can handle a partially filled tray without the risk of ingots falling out of cells 114.

To remove an ingot from a tray 102, a user can apply a force directly to an ingot from the underside of the retaining surface 104, through the bottom of a cell 114 between transverse members 120, causing laterally adjacent tabs 602 to momentarily flex away from the lateral centerline of a cell 114 and release an ingot.

Figure 7:
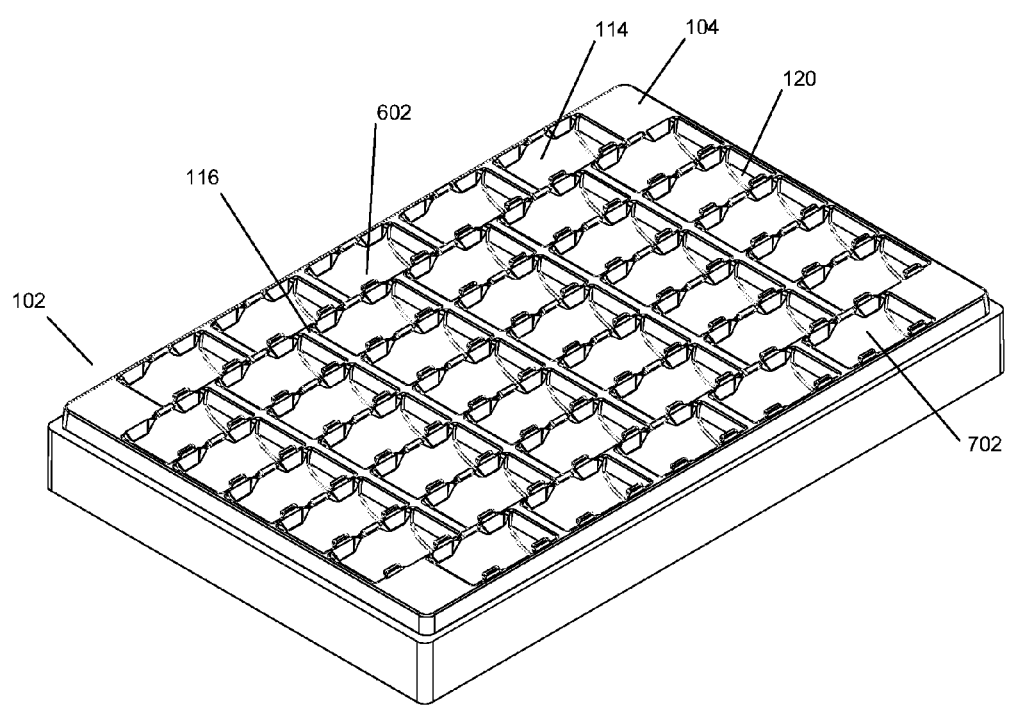
FIG. 7 depicts a perspective view of another embodiment of a tray used in the present system.
Figure 7A:
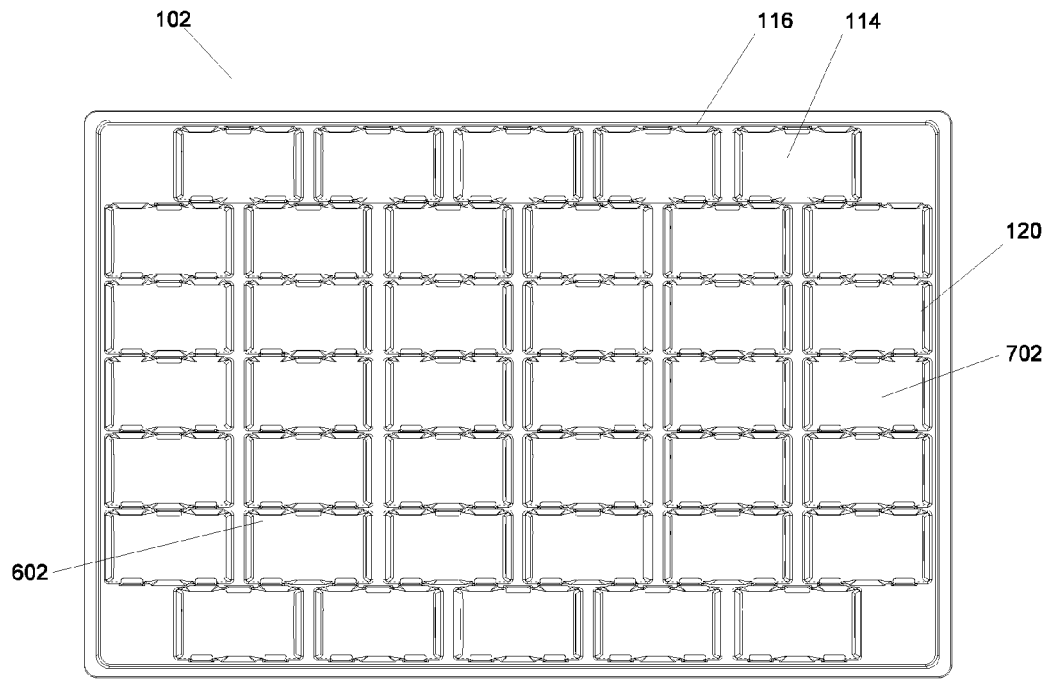
FIG. 7a depicts top planar view of the embodiment of a tray used in the present system as shown in FIG. 7.

FIG. 7 depicts a perspective view of another embodiment of a tray that can be used in the present system. In some embodiments, as shown in FIGS. 7 and 7a, at least two pairs of laterally adjacent tabs 602 can extend from the top edge of a substantially parallel longitudinal member 116 with each extending toward the interior of a laterally adjacent cell 114.

As shown in FIG. 7, each laterally adjacent tab 602 can have an angle of approximately 45-degrees and/or any other known, convenient and/or desired angle while extending above the top of a retaining surface 104, but in other embodiments can be positioned at any other known and/or convenient angle. In some embodiments one or more of the tabs 122 can be adapted and designed to have any desired length and/or flexibility and/or stiffness relative to a longitudinal member 116 and/or any other known and/or convenient element and/or item. In some embodiments, a laterally adjacent tab 602 can have a thickness substantially similar to that of a substantially parallel longitudinal member 116. In some embodiments, as shown in FIG. 7, a laterally adjacent tab 602 can have a substantially rounded top edge, but in other embodiments can have any other known and/or convenient geometry.

Figure 7B:
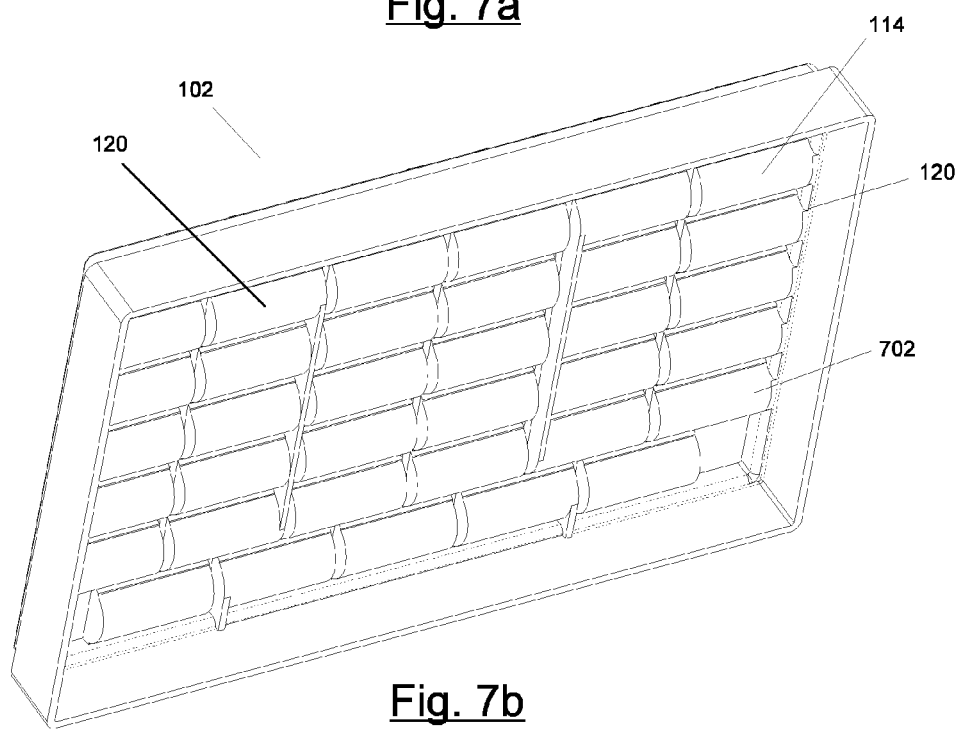
FIG. 7b depicts a perspective bottom view of the embodiment of a tray used in the present system as shown in FIG. 7.
Figure 7C:
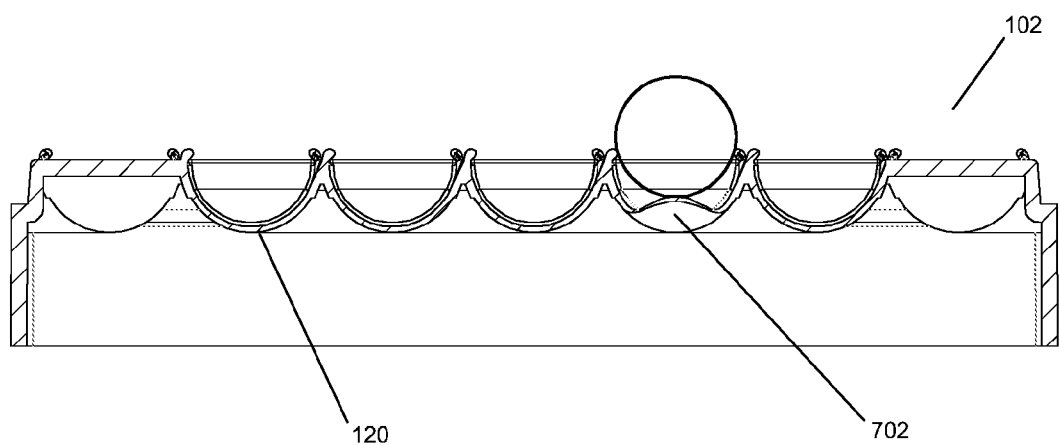
FIG. 7c depicts a detail transverse cross-sectional view of the embodiment shown in FIG. 7.

In the embodiment shown in FIGS. 7 and 7b, a transverse member 120 can substantially completely enclose the underside of cell 114. As shown in FIG. 7c, in some embodiments, a transverse member 120 can further comprise a thinned section 702 substantially along the longitudinal axis of a transverse member 120. In response to a force, a thinned section 702 can deform more easily than the surrounding regions.

In use, an ingot can be placed into a cell 114 such that laterally adjacent tabs 602 hold an ingot in place. In embodiments such as those shown in FIG. 7, in which a cell 114 can be configured to hold a substantially cylindrical ingot, an ingot can rest in horizontally in a cell 114 such that substantially half of an ingot lies below the top edge of a cell 114 and laterally adjacent tabs 602 can slant inward to hold an ingot in place by extending above the top edge of a cell 114 and substantially adjacent to the surface of an ingot.

To remove an ingot from the tray, a user can apply a force to a thinned section 702 of a transverse member 120, and thereby to an ingot, causing laterally adjacent tabs 602 to momentarily flex outward and release an ingot as a substantially upward force is applied to said ingot.

Figure 8:
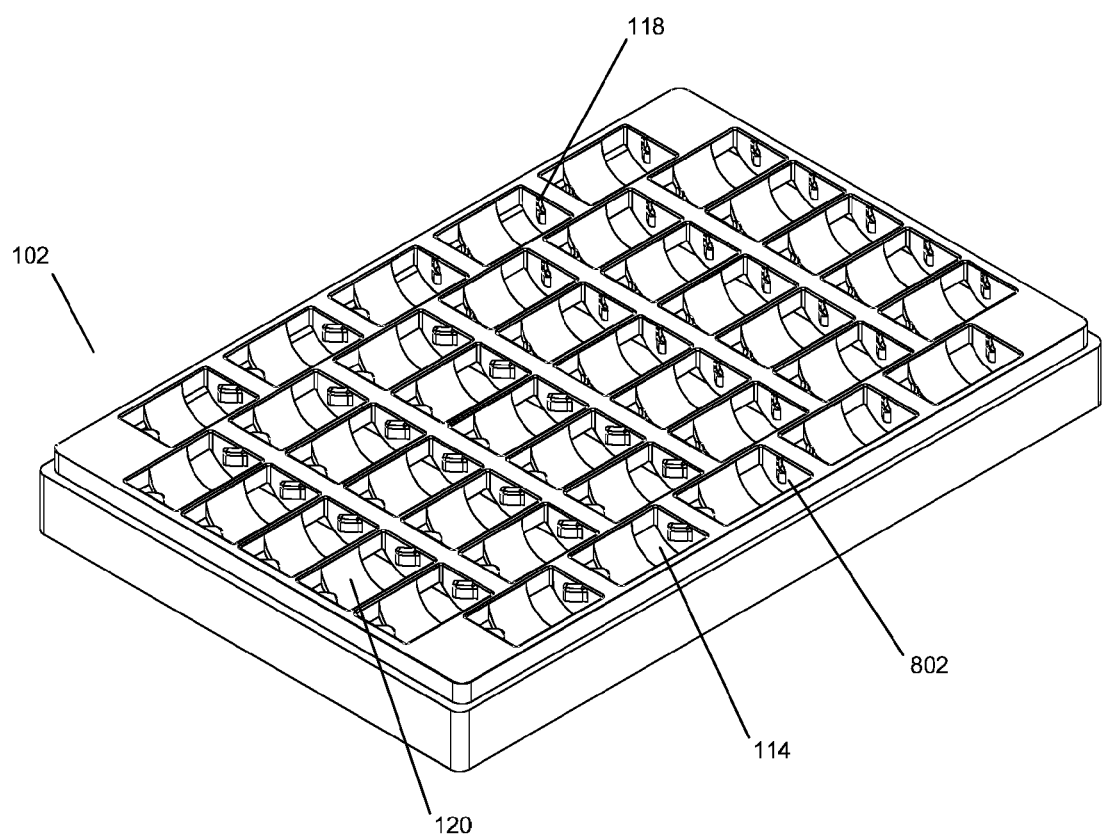
FIG. 8 depicts a perspective view of another embodiment of a tray used in the present system.

FIG. 8 depicts a perspective view of another embodiment of a tray that can be used in the present system. In some embodiments, a single transverse member 120 can be located substantially across the longitudinal midpoint of a cell 114. In some embodiments, a transverse member 120 can have a width not exceeding approximately half of the length of a cell 114.

Figure 8A:
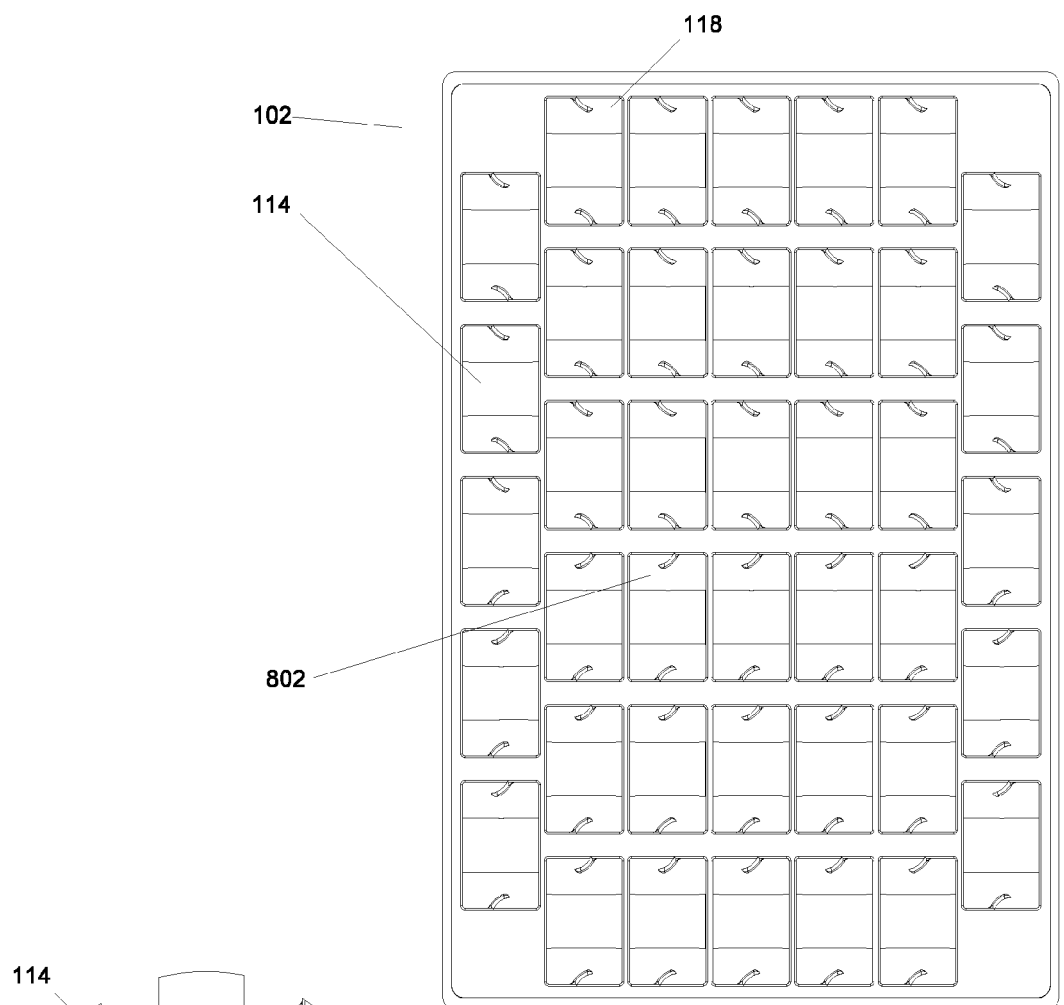
FIG. 8a depicts top planar view of the embodiment of a tray used in the present system as shown in FIG. 8.
Figure 8B:
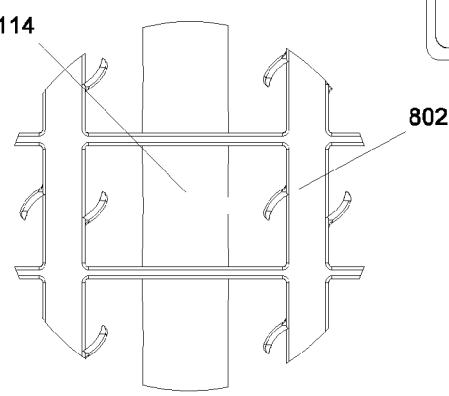
FIG. 8b depicts a detail view of the embodiment of a tray used in the present system as shown in FIG. 8.
Figure 8C:
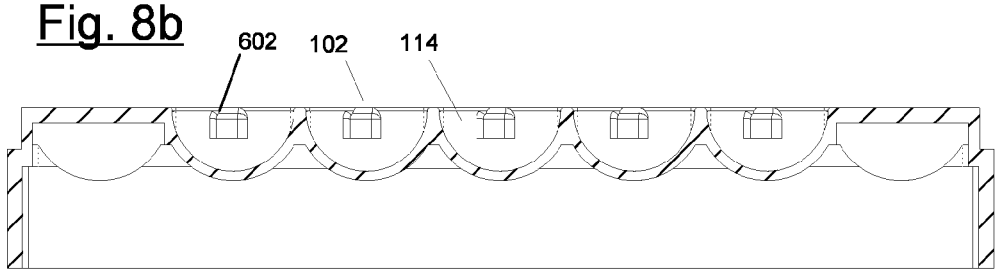
FIG. 8c depicts a detail transverse cross-sectional view of the embodiment shown in FIG. 8.

In some embodiments, as shown in FIG. 8a and in more detail in FIG. 8b, at least one end member 118 of a cell 114 can have at least one protrusion 802. In some embodiments, a protrusion 802 can be configured as a curved hook, the curved portion of which can be oriented substantially parallel to a retaining surface 104 and can extend laterally in approximately a ninety-degree arc, or any other known and/or convenient length. In embodiments having a protrusion 802 on extending from each end member 118, protrusions 802 can be oriented such that the free end of each protrusion 802 can extend toward opposite lateral sides of a cell 114.

Figure 9:
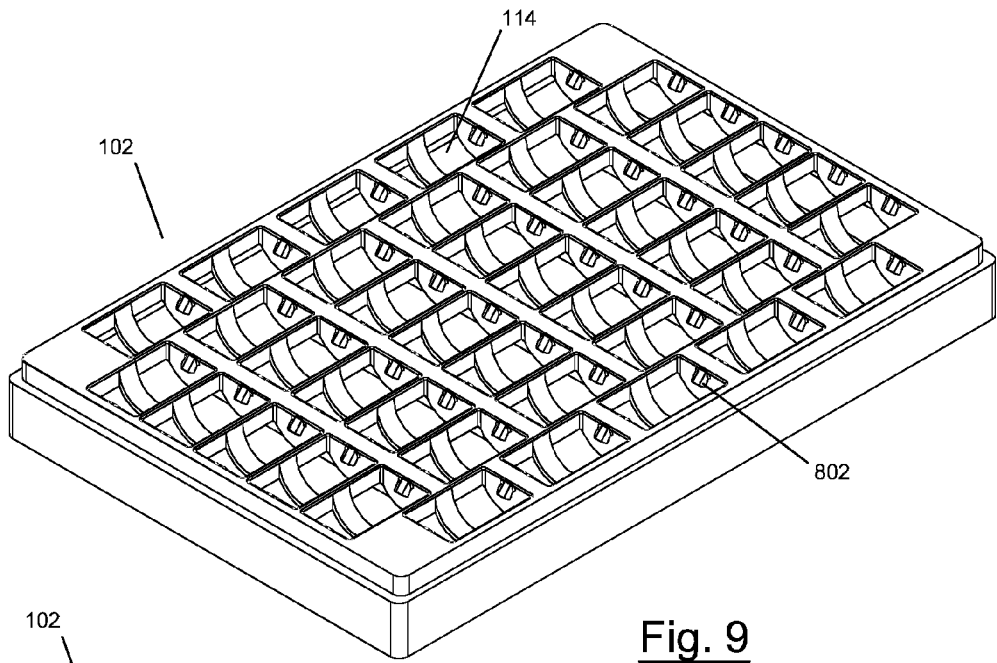
FIG. 9 depicts a perspective view of another embodiment of a tray used in the present system.
Figure 9A:
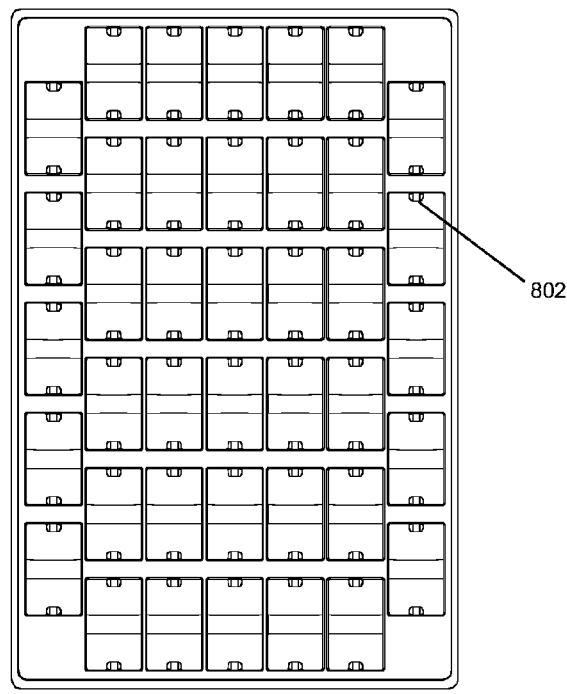
FIG. 9a depicts top planar view of the embodiment of a tray used in the present system as shown in FIG. 9.
Figure 9B:
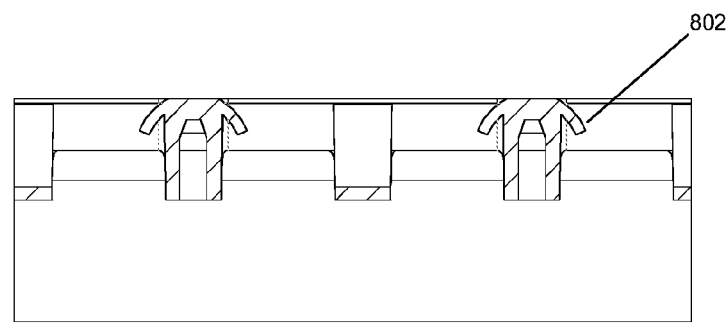
FIG. 9b depicts a detail view of the embodiment of a tray used in the present system as shown in FIG. 9.
Figure 9C:
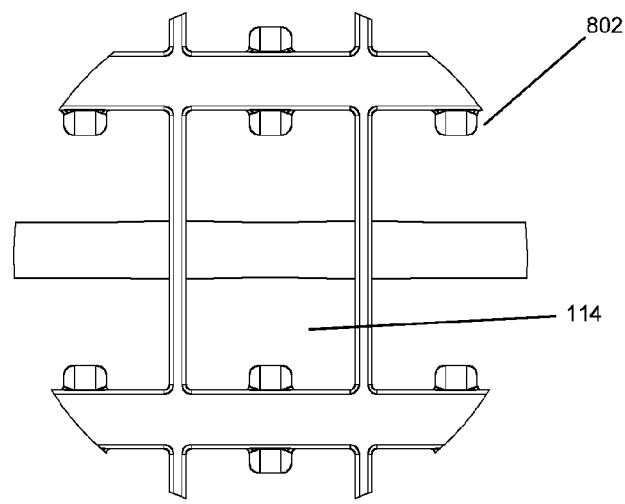
FIG. 9c depicts a detail view of the embodiment of a tray used in the present system as shown in FIG. 9.
Figure 9D:
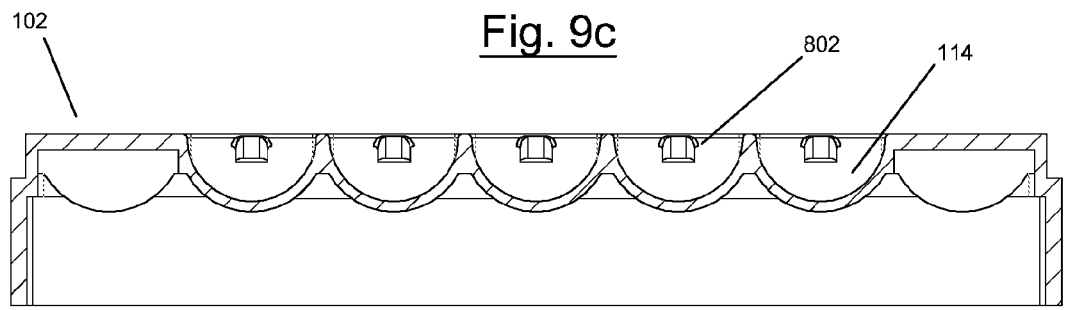
FIG. 9d depicts a detail transverse cross-sectional view of the embodiment shown in FIG. 9.

FIG. 9 depicts a perspective view of another embodiment of a tray 102 that can be used in the present system. In some embodiments, at least one protrusion 802 can be a downward-oriented hook. As shown in FIG. 9, in embodiments having a protrusion 802 at each end of a cell 114, both protrusions 602 can be pointed into a cell 114, but in other embodiments can be pointing opposite directions or in any other known and/or convenient orientation relative to each other.

Figure 10:
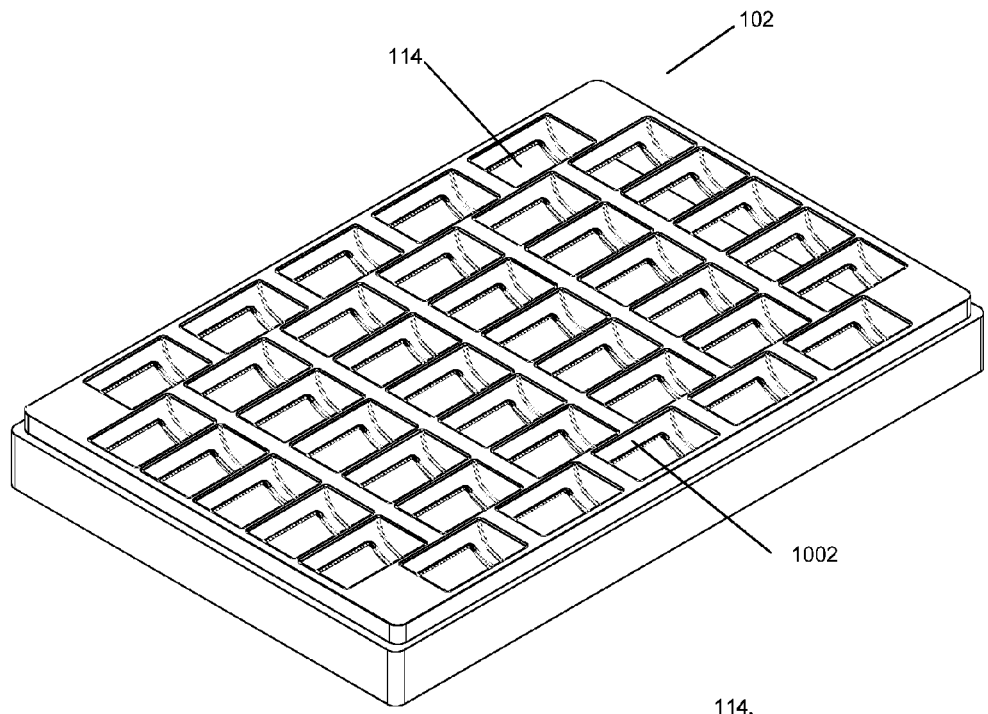
FIG. 10 depicts a perspective view of another embodiment of a tray used in the present system.
Figure 10A:
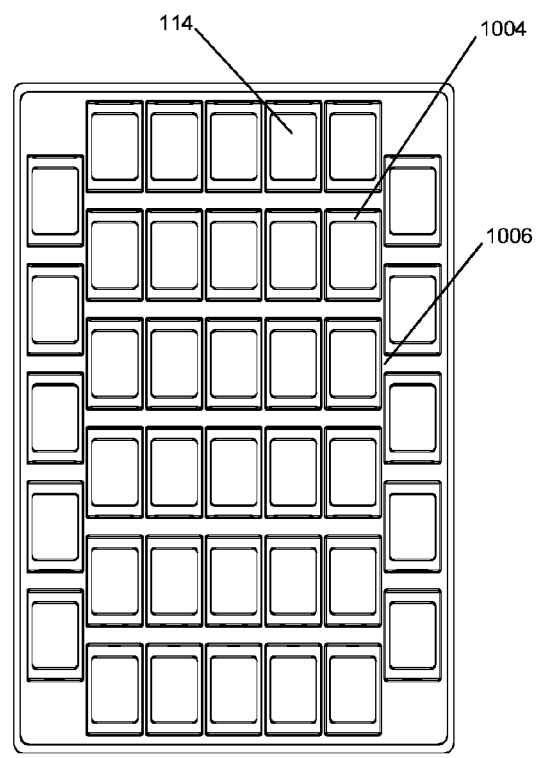
FIG. 10a depicts top planar view of the embodiment of a tray used in the present system as shown in FIG. 10.
Figure 10B:
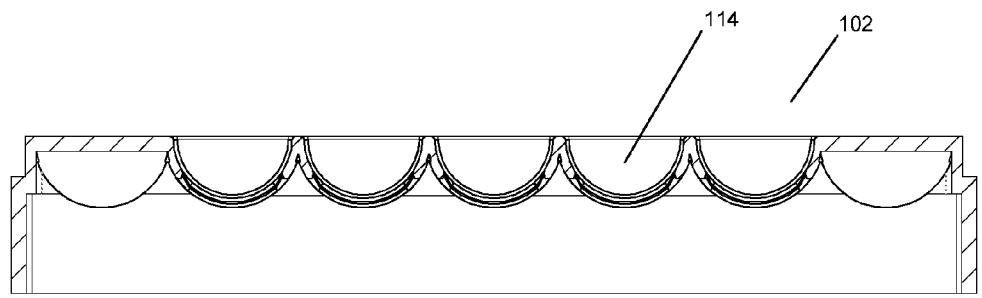
FIG. 10b depicts a detail transverse cross-sectional view of the embodiment shown in FIG. 10.

FIG. 10 depicts a perspective view of another embodiment of a tray 102 that can be used in the present system. In some embodiments, the bottom of a cell 114 can comprise a bottom member 1002 that can extend inward around the lower perimeter of a cell 114. End segments 1004 of a bottom member 1002 having a configuration as shown in FIG. 10 can have a width less than that of half of the length of a cell 114 or any other known and/or convenient dimension. Lateral segments 1006 can have a width less than that of half of the width of a cell 114 or any other known and/or convenient dimension. In some embodiments, end segments 1004 and lateral segments 1006 can have different widths, but in other embodiments can have a uniform width around the perimeter of a base member 1002.

Figure 10C:
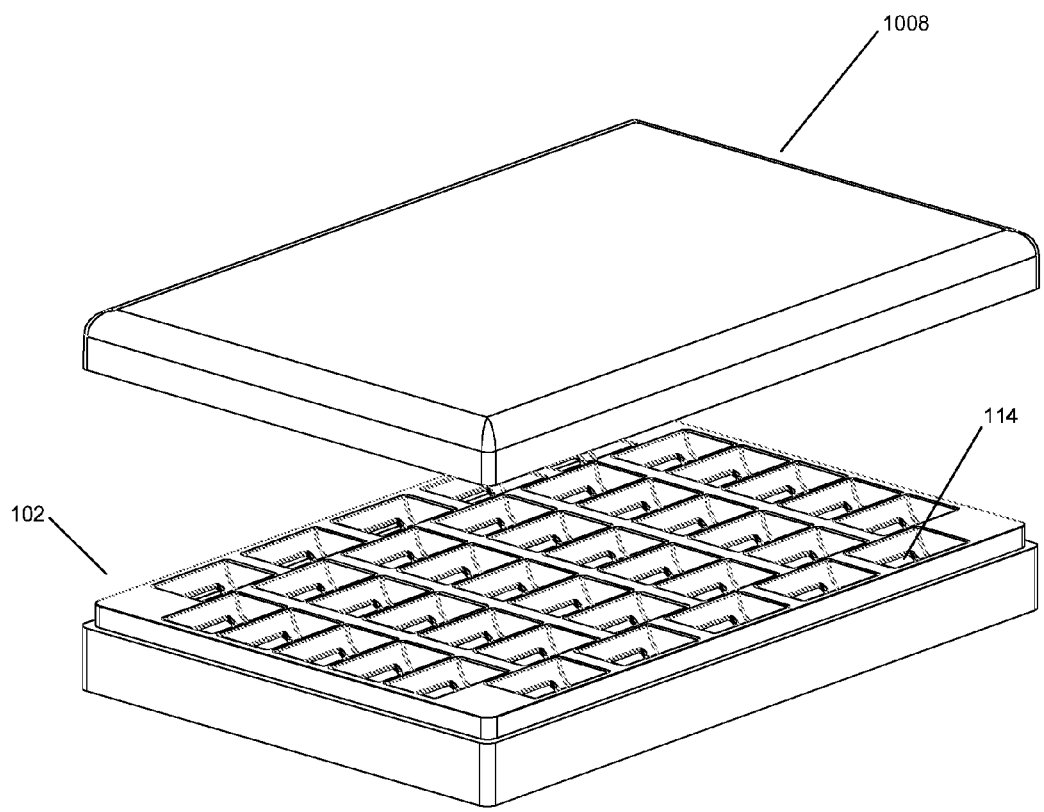
FIG. 10c depicts a perspective view of another embodiment of the tray shown in FIG. 10.

In some embodiments, as shown in FIG. 10, a cell 114 can lack a retaining feature, such as, but not limited to protrusions 802 and tabs 122 602. As shown in FIG. 10c, in such embodiments, a tray 102 can further comprise a lid 1008 that can selectively engage with a tray 102 to cover a retaining surface 104. In some embodiments, a lid 1008 can selectively engage with a tray 102 by a friction fit, latch system, or any other known and/or convenient mechanism.

Figure 11:
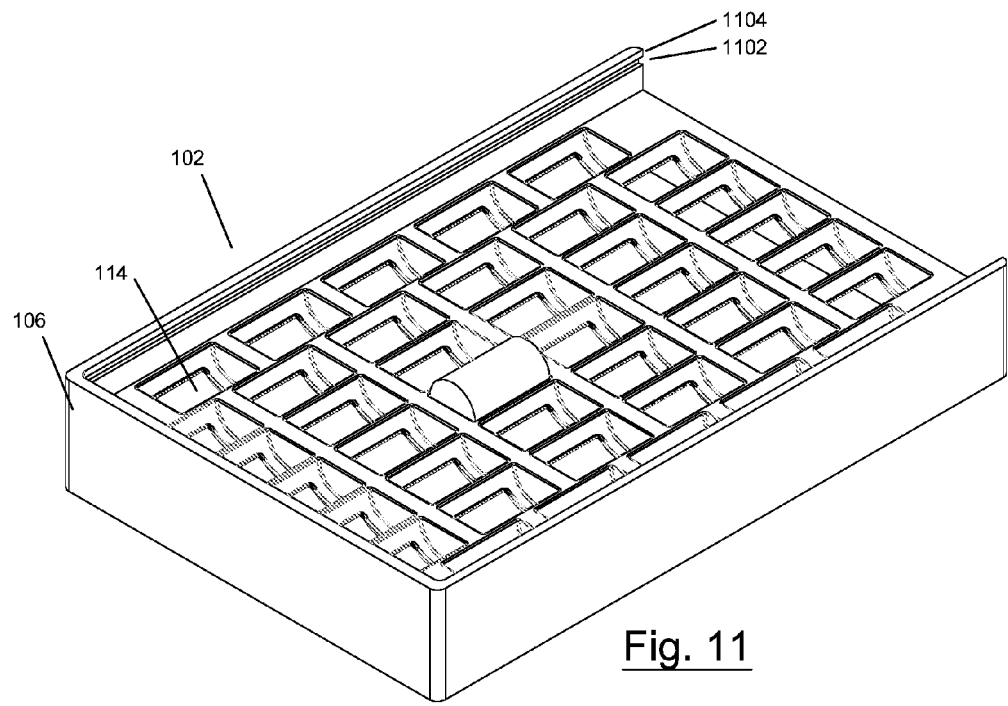
FIG. 11 depicts a perspective view of another embodiment of a tray used in the present system.
Figure 11A:
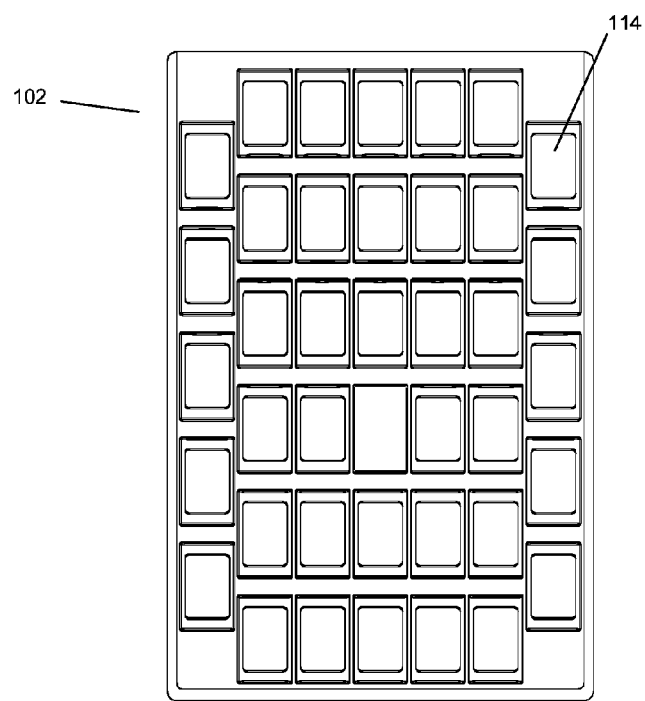
FIG. 11a depicts top planar view of the embodiment of a tray used in the present system as shown in FIG. 11.
Figure 11B:
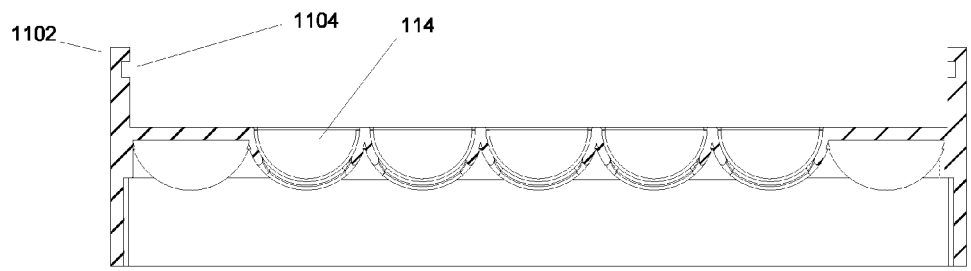
FIG. 11b depicts a detail transverse cross-sectional view of the embodiment shown in FIG. 11.
Figure 11C:
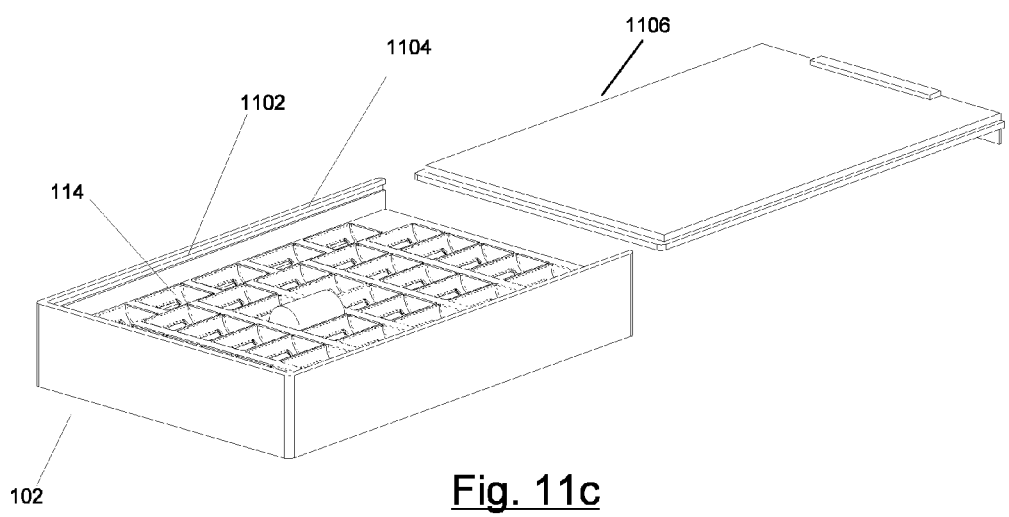
FIG. 11c depicts a perspective view of another embodiment of the tray shown in FIG. 11.

FIG. 11 depicts a perspective view of another embodiment of the present device. As shown in FIG. 11, some embodiments can have an upward extension 1102 of at least two substantially parallel segments of a wall 106 above a retaining surface 104. In the embodiment shown in FIG. 11, extensions 1102 can exist of each of the lateral segments and one end segment of a wall 106. A channel 1104 can be cut into the interior surface of an extension 1102, parallel to the top edge of an extension 1102 and at a distance from the top of a retaining surface 104 of a tray 102 substantially equivalent to slightly more than the radius of an ingot, whether cylindrical and/or having any other known and/or convenient geometry. A lid 1106 can selectively engage with a tray 102 via a channel 1104 and hold ingots securely in cells 114.

Figure 12:
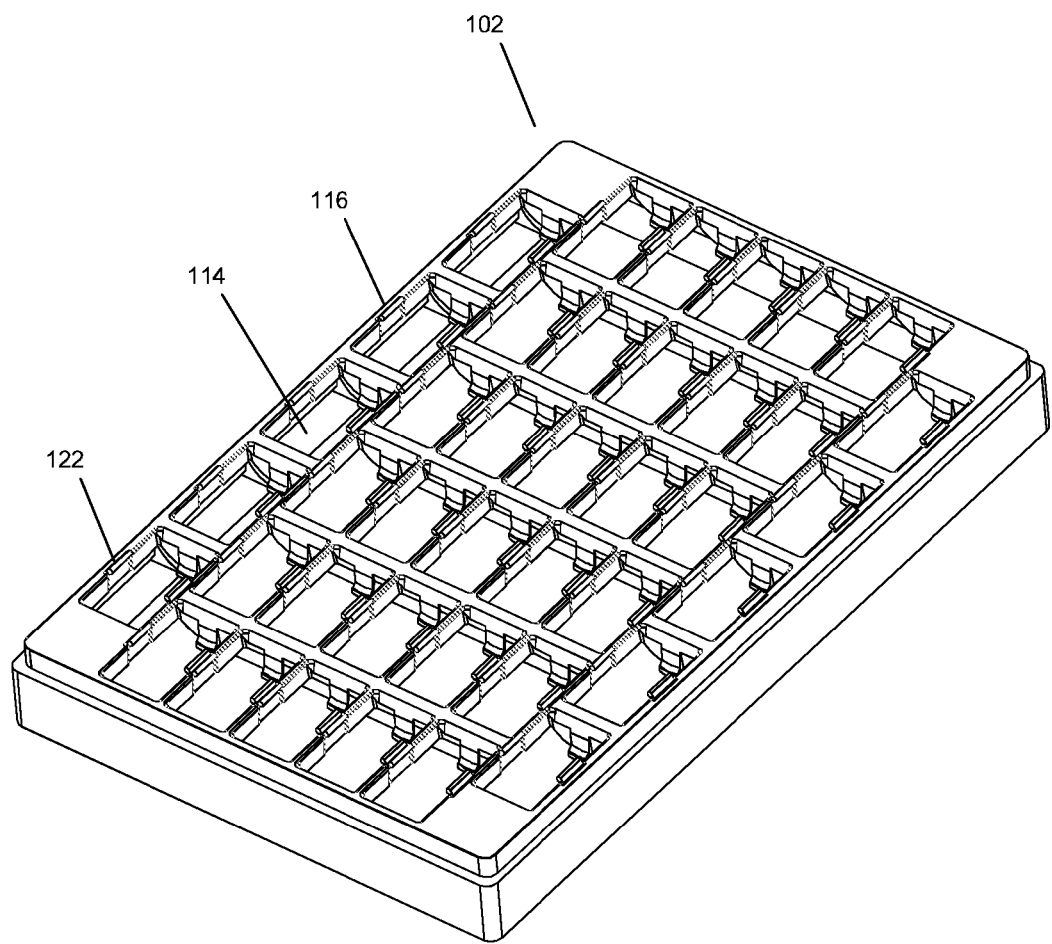
FIG. 12 depicts a perspective view of another embodiment of a tray used in the present system.
Figure 12A:
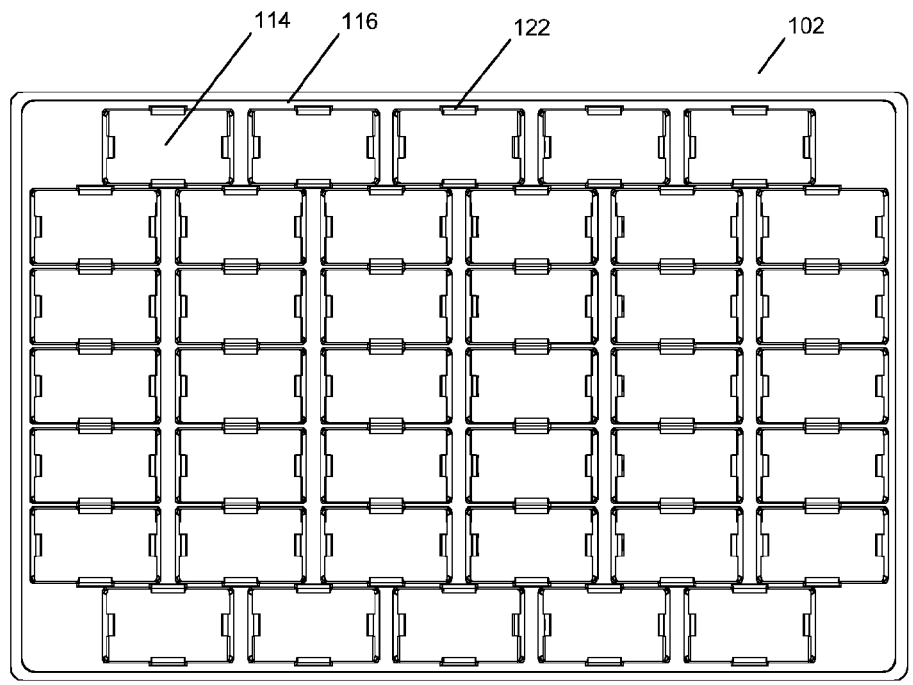
FIG. 12a depicts a top planar view of the embodiment of a tray used in the present system as shown in FIG. 12.
Figure 12B:
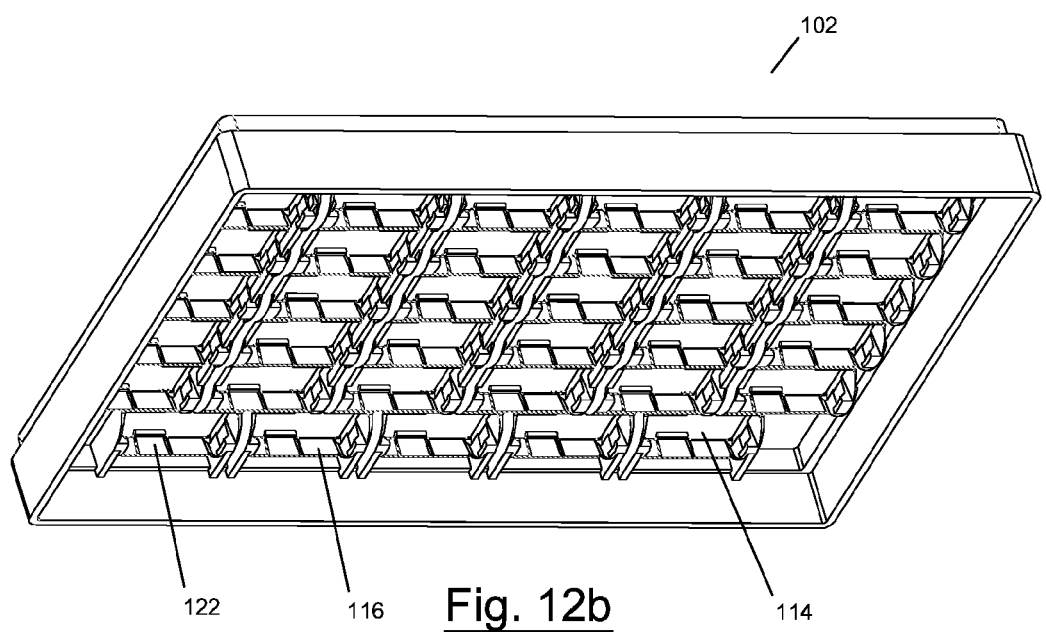
FIG. 12b depicts a perspective bottom view of the embodiment of a tray used in the present system as shown in FIG. 12.
Figure 12C:
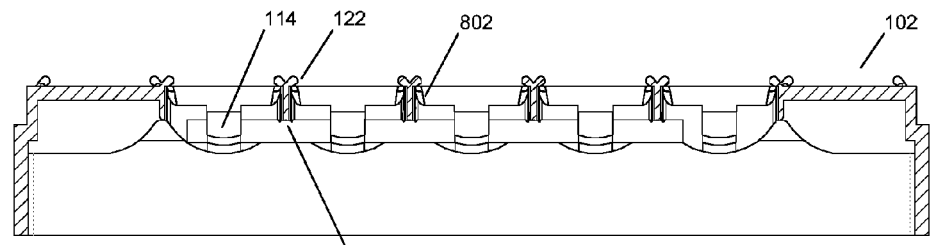
FIG. 12c depicts a detail transverse cross-sectional view of the embodiment shown in FIG. 12.
Figure 12D:
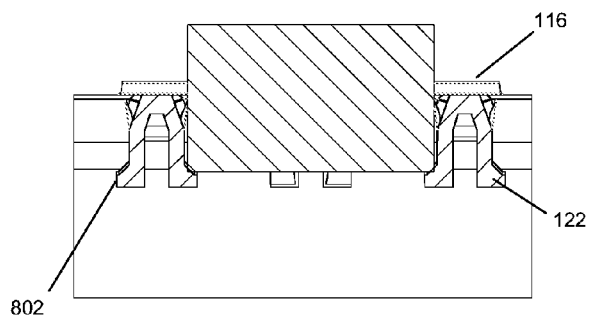
FIG. 12d depicts a detail view of another embodiment of the tray shown in FIG. 12.

FIG. 12 depicts a perspective view of another embodiment of a tray 102 that can be used in the present system. In some embodiments, as shown in FIG. 12, a cell 114 can comprise both tabs 122 along the top edge of a longitudinal member 116 and protrusions 802 from an end member 118 that can serve as retention hooks to hold an ingot in a cell 114.

In some embodiments, an ingot can be inserted from top of the device until it seats on protrusion 802. In some embodiments, a fixture below (not shown) can help prevent accidental over-insertion. In some embodiments, the fixture below (not shown) may not be present. Once ingot is placed in cell 114, tab 122 can prevent the ingot from falling out of the top if tray 102 is inverted. In some embodiments, protrusion 802 can prevent accidental falling out of the ingots at the bottom. Thus, to eject an Ingot press from the tray 102, a user or machine can press on top of ingot to pop ingot out of bottom of the tray 102. In such embodiments, protrusion 802 can deflect and release the ingot from the tray 102.

Figure 12E:
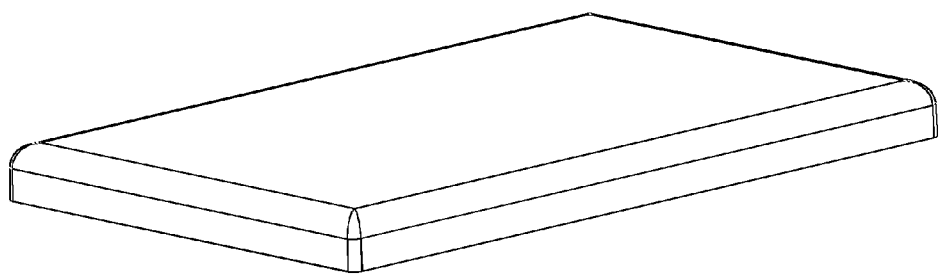
FIG. 12e depicts a perspective view of another embodiment of the tray shown in FIG. 12.
Figure 12E:
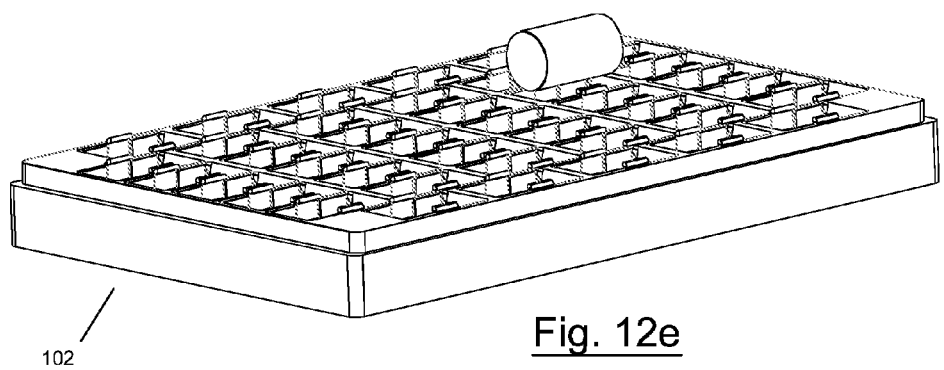

In alternate embodiments, as shown in FIG. 12e, a tray 102 can further comprise a lid 1008 that can selectively engage with a tray 102 to cover a retaining surface 104. In some embodiments, a lid 1008 can selectively engage a tray 102 by a friction fit, latch system, or any other known and/or convenient mechanism.

Figure 13:
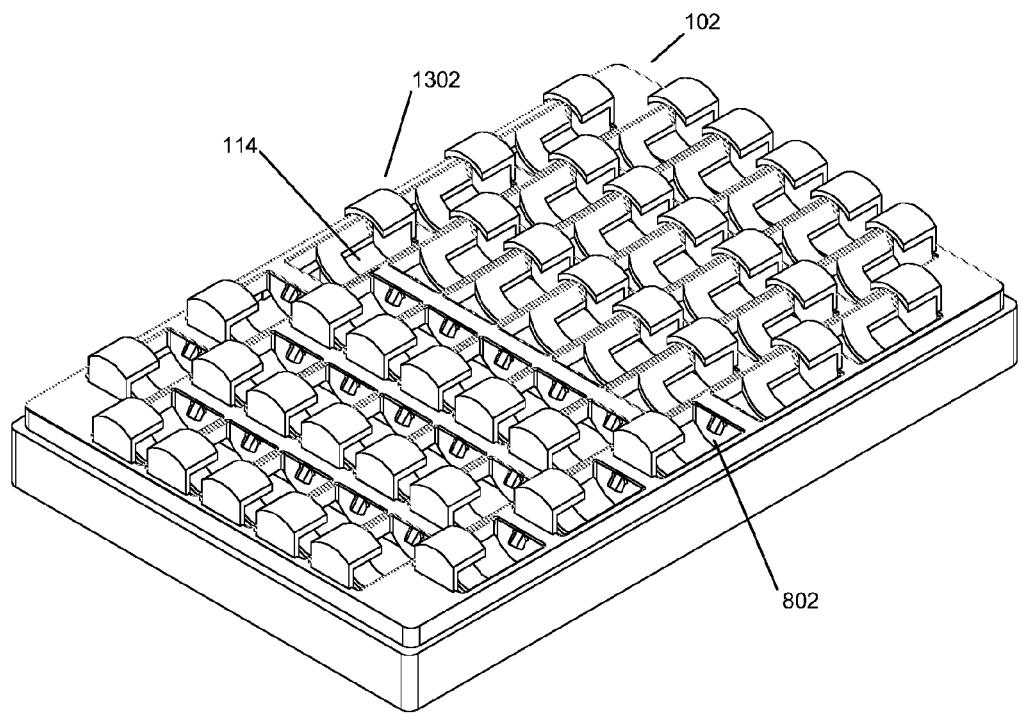
FIG. 13 depicts a perspective view of another embodiment of a tray used in the present system.
Figure 13A:
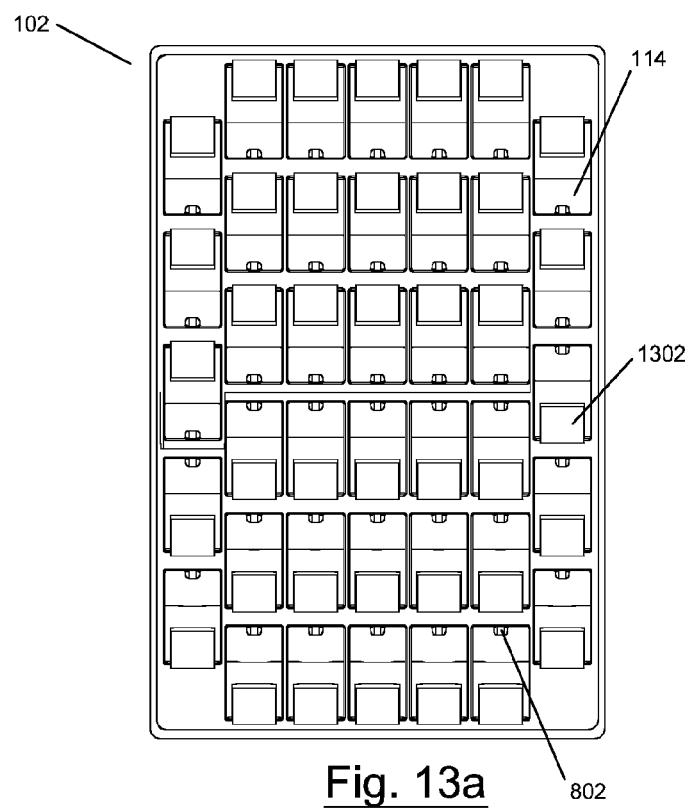
FIG. 13a depicts a top planar view of the embodiment of a tray used in the present system as shown in FIG. 13.
Figure 13B:
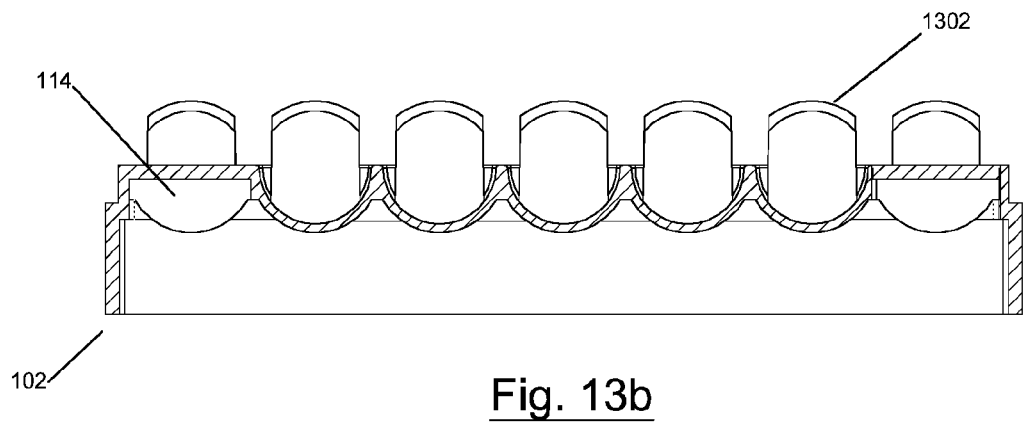
FIG. 13b depicts a detail transverse cross-sectional view of the embodiment shown in FIG. 13.
Figure 13C:
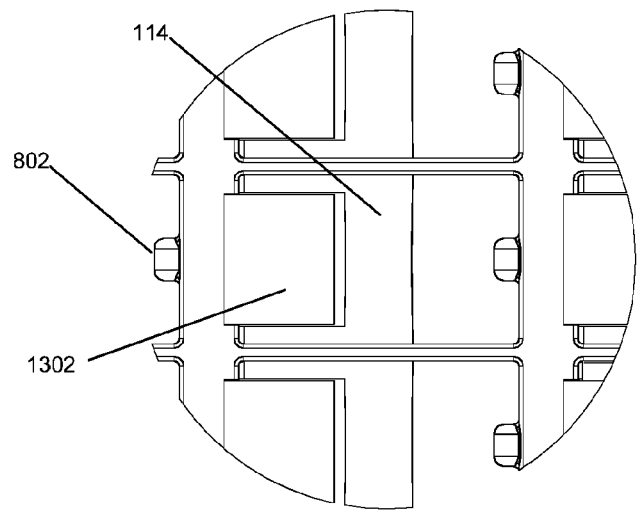
FIG. 13c depicts a detail view of another embodiment of the tray shown in FIG. 13.
Figure 13D:
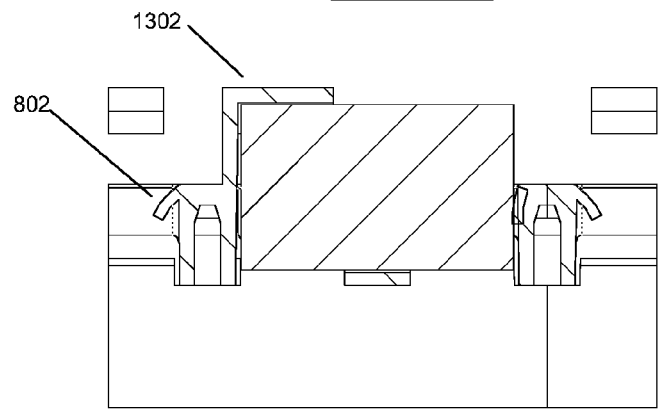
FIG. 13d depicts a detail view of another embodiment of the tray shown in FIG. 13.

FIG. 13 depicts a perspective view of another embodiment of a tray 102 that can be used in the present system. In some embodiments, a cell 114 can further comprise a partial end cap 1302 that can extend over the open top of a cell 114. As shown in FIG. 13, a partial end cap 1302 can have an L-shaped configuration and extend from one end of a cell 114. In some embodiments, the top member of a partial end cap 1302 can be configured to selectively engage with an ingot surface. As shown in FIG. 13, this can be a curved ingot retention surface to retain a substantially cylindrical ingot, but in other embodiments can have any other known and/or convenient geometry.

As shown in FIG. 13, a transverse member 120 can enclose a desired portion of the bottom of a cell 114, starting at the same end from which a partial end cap 1302 extends. In some embodiments, a protrusion 802, which can be a downward pointing hook, can extend from the opposite end of a cell 114.

In some embodiments, traverse member 120 is in the mid section of cell 114 and connects to the longitudinal members 116 so that the partial end cap 1302 on one end and the protrusion 802 can be formed from the underside by the injection mold.

In using an embodiment as shown in FIG. 13, an ingot can be placed into a cell 114 such that one end rests under a partial end cap 1302 and a protrusion 802 deflects, and the resulting tension in a protrusion 802 can help to hold an ingot securely in a cell 114. To release an ingot, a user can press an ingot upward from the underside of a tray via the open portion of the bottom of a cell 114. In some embodiments the user can press from the underside of the cell 114 at the side of the protrusion 802.

Although the method has been described in conjunction with specific embodiments thereof, it is evident that many alternatives, modifications and variations will be apparent to those skilled in the art. Accordingly, the method as described and hereinafter claimed is intended to embrace all such alternatives, modifications and variations that fall within the spirit and broad scope of the appended claims.

What is claimed is:

1. A system and method for producing, marking, and packaging ingots, comprising the steps of:
   introducing ingots to a production line via a first feeding mechanism;
   inspecting ingots for conformance to desired weight, size, and cosmetic requirements;
   transporting ingots to a second feeding mechanism;
   introducing a plurality of trays into said production line;
   inserting ingots into said trays;
   weighing said filled trays to check compliance with a desired weight range;
   marking said ingots;
   optically inspecting said ingots;
   inserting said loaded ingot trays into a packaging unit;
   packaging said loaded ingot trays;
   weighing said packaged trays for check compliance with a desired weight range;
   placing a wrapping on the exterior of said packaged trays;
   sending said wrapped package to a master packaging station, wherein a plurality of wrapped packages are combined into a larger unit;
   placing a wrapping on the exterior of said larger unit;
   combining a plurality of larger units into a pallet box for shipping.

2. The system of claim 1, wherein said marking is accomplished by a method selected from the list consisting of: inkjet printing, pad printing, stamping, etching, and engraving.

3. The system of claim 1, wherein a tray further comprises:
   a base member having a vertical wall extending substantially perpendicularly downward from the perimeter of a substantially planar member;

a plurality of adjacent openings in said substantially planar member, each opening connected to at least one bottom member to form a compartment, and each compartment separated by a lateral wall.

4. The tray of claim 3, wherein compartment has a substantially semicircular cross-section.

5. The tray of claim 3, wherein said compartment has a substantially open bottom.

6. The tray of claim 5, further comprising a plurality of tabs extending from the top edge of said lateral compartment walls.

7. The tray of claim 6, wherein said tabs are configured with three tabs extending from each lateral compartment wall, alternately such that two tabs extend slightly over the lateral edge of one compartment, while the third tab, between the first two tabs, extends slightly over the adjacent lateral edge of a laterally adjacent compartment.

8. The tray of claim 6, wherein a pair of adjacent tabs extend from substantially the middle portion of a lateral compartment wall, each tab extending over the adjacent lateral edge of a laterally adjacent compartment.

9. The tray of claim 8, wherein said tabs extend upward at an angle of approximately 45 degrees with respect to a top surface.

10. The tray of claim 5, wherein said compartment further comprises at least one protrusion extending into a compartment from and end surface of said compartment.

11. The tray of claim 10, wherein said protrusion is a hook oriented concave down with respect to the end of a compartment from which a protrusion extends.

12. The tray of claim 5, further comprising an L-shaped partial end cap extending substantially perpendicularly from a top surface of a tray and over the open top of a compartment.

13. The tray of claim 3, wherein the longitudinal median section of a bottom member is more easily deformable than the remainder of a bottom member.

14. The tray of claim 3 or 5, further comprising a lid capable of selectively engaging with said base member.

* * * * *